US012752068B2

(12) United States Patent
Luo

(10) Patent No.: US 12,752,068 B2
(45) Date of Patent: Oct. 6, 2026

(54) FRAME ASSEMBLY FOR A VENTILATOR TO DELIVER GAS

(71) Applicant: DCSTAR INC., New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/540,221

(22) Filed: Dec. 14, 2023

(65) Prior Publication Data

US 2025/0195814 A1 Jun. 19, 2025

(51) Int. Cl.
*A61M 16/06* (2006.01)
*A61M 16/08* (2006.01)
*A61M 16/20* (2006.01)

(52) U.S. Cl.
CPC .... *A61M 16/0683* (2013.01); *A61M 16/0622* (2014.02); *A61M 16/0633* (2014.02); *A61M 2210/0612* (2013.01); *A61M 2210/0618* (2013.01)

(58) Field of Classification Search
CPC .......... A61M 16/0683; A61M 16/0622; A61M 2210/0612; A61M 2210/0618; A61M 16/0633–0655; A61M 16/06–0627; A61M 16/08–0875
See application file for complete search history.

(56) References Cited

U.S. PATENT DOCUMENTS

2004/0226566 A1* 11/2004 Gunaratnam ..... A61M 16/0825 128/207.18
2009/0107508 A1* 4/2009 Brambilla ......... A61M 16/0644 128/207.11
2013/0199537 A1* 8/2013 Formica ............ A61M 16/0683 128/205.25
2016/0263338 A1* 9/2016 Borsari ................. A61M 16/06
2019/0022343 A1* 1/2019 Kooij ................ A61M 16/0883
2020/0061398 A1* 2/2020 Rummery ......... A61M 16/0622
2022/0296837 A1* 9/2022 Law .................. A61M 16/0816
2022/0379061 A1* 12/2022 Kooij ................ A61M 16/0611

* cited by examiner

*Primary Examiner* — Valerie L Woodward
*Assistant Examiner* — Mautin I Ashimiu
(74) *Attorney, Agent, or Firm* — HSML P.C.

(57) ABSTRACT

A frame assembly for a ventilator to deliver gas includes: a frame with a first interface set on the patient's forehead, a second interface near a nasal side of the patient, and a hollow tube; wing elements, to connect to a headgear to secure the frame on the patient's face, having a first wing element and a second wing element. The hollow tube extends from the patient's first nasal side, ascends towards the first temporal region, further rises to the forehead, then extends to the second temporal region and reaches the second nasal side, to form a contour that at least partially encircles the patient's eyes and nose. A support portion, set on an inner wall of the hollow tube, is to prevent the gas delivery device from bottoming out.

20 Claims, 21 Drawing Sheets

FRAME ASSEMBLY FOR A VENTILATOR TO DELIVER GAS

TECHNICAL FIELD

This disclosure relates to a device for delivering the breathing gas for the treatment to a patient's airway, specifically pertaining to a frame assembly with a hollow tube for gas delivery, which is connectable to a patient interface cushion.

BACKGROUND

Sleep is an essential part of daily life, occupying roughly one-third of our time. Sleep quality and quantity play a critical role in numerous brain functions and contribute to the rejuvenation of the immune, neurological, skeletal, and muscular systems. However, some individuals suffer from sleep disorders, including insomnia, sleep apnea, and hypersomnia, leading to compromised sleep quality or chronic sleep deprivation, further triggering concentration difficulties, delayed reactions, a compromised immune system, and an increased risk of cardiovascular diseases, hypertension, and diabetes, among other health issues. To safeguard quality sleep, patients require consistent care or treatment. One prevalent therapeutic approach for patients with sleep apnea is Positive Airway Pressure (PAP), specifically in the form of Continuous Positive Airway Pressure (CPAP). CPAP entails transmitting positive breathing gas from a flow generator into the patient's airway for sleep-associated breathing disorders. Equipment used in CPAP therapy typically includes a flow generator, a gas delivery device, and a mask system. The mask system itself can be categorically divided into three primary components: the frame assembly, the headgear, and the patient interface cushion. The patient interface cushion ensures a sealed connection to the patient's airway, while the frame assembly and the headgear work together to secure the patient interface cushion onto the patient's head, guaranteeing that the pressurized airflow is transmitted into the patient's airway.

Beyond the patient interface cushion, the frame assembly makes the most extensive contact with the face of the patient, making the comfort of wearing the frame paramount. Furthermore, the design for the frame should not impede the patient's daily life. While ensuring comfort and aesthetic appeal, additional functionalities within the frame assembly can be supplemented. In the current market, there are several common types of frames. For example, frames with forehead supports offer improved stability and help to distribute the pressure from the mask system away from the nose bridge; frames with bilateral connectors, which avoid the upper portion of the patient's face, offering a clearer field of vision and compatibility with eyeglasses. Manufacturers have made modifications to enhance the frame's comfort, such as using gel materials for the frame or adding fabric coverings to the frame. Despite these advancements, issues like facial pressure and discomfort persist. Besides, the conventional design of frames often situates the gas interface at the center, which means that when connected to the gas delivery device, the breathing tube extends from the patient's nose toward the neck, creating potential issues with tangling and knotting during sleep turnovers and head movements.

Recently, a novel frame design has debuted on the market, made from elastomeric material, with a hollow tube for gas delivery that extends from the patient's nasal sides up to the top of the head. This design alleviates facial pressure, offering a more comfortable experience.

SUMMARY

The upper part of the frames with frontal support is usually larger and heavier, which is not ideal for patients who need to wear glasses. Nevertheless, to ensure stability at the connectors, the frames with bilateral connectors use rigid or semi-rigid materials that can cause the connector to press the face which further causes pressure sores and red marks when a patient is lying on his or her side. The existing novel frames place the gas interface atop the head, and stability is solely reliant on two headgear connection points situated above the ears. This means that there is no external force around the patient interface cushion other than its own gravity and the pulling force exerted by the frame at the connection point on the frame. While this design of the frames maintains a relative balance when the patient's head is upright, during sleep, the weight of the frame, compounded by the attached gas delivery device, poses a risk of slippage from the patient's head, primarily due to the lack of adequate support. Such a slippage will affect the location of the patient interface cushion, further compromising the efficacy of the therapy.

Disclosed and recited herein is a frame assembly that is more comfortable than conventional frame assemblies and more stable than known frames.

In one embodiment, this disclosure discloses a frame assembly for a ventilator to deliver gas, configured to deliver positive pressure breathing gas from a flow generator to a patient's airway for the treatment of sleep breathing disorders, the frame assembly for a ventilator to deliver gas including at least some of the following elements or features.

A frame has a first interface and two second interfaces, with the first interface set on the forehead of the patient to receive positive pressure breathing gas and the second interfaces near both nasal sides of the patient.

The frame has a symmetrical hollow tube, connectable to the first interface positioned at the center of the frame and to the second interfaces on each nasal side of the patient, to deliver positive pressure breathing gas from the first interface to the second interfaces. The hollow tube has a front wall, a back wall, an inner edge and an outer edge formed at the junction of the front wall and the back wall.

Wing elements are configured to connect to a headgear to secure the frame on the patient's face, including a first wing element on the outer edge of the hollow tube near the first interface, and a second wing element on the outer edge of the hollow tube near the second interface.

The hollow tube extends from a first nasal side of the patient, ascends towards a first temporal region, further rises to the forehead, then extends to a second temporal region, and finally reaches a second nasal side of the patient, forming a contour that at least partially encircles the patient's eyes and nose.

In one embodiment, the wing elements are integrally formed with the frame and are made of silicone with a hardness of at or between 30 A to 70 A on a Shore scale.

In one embodiment, the first wing element has at least one opening to connect to the headgear, and the second wing element has at least one opening to connect to a quick-release component.

In one embodiment, the frame assembly can include an automatic adjustment mechanism, located on the hollow tube near the first interface of the frame, to automatically adapt the length or width of the hollow tube to accommodate the facial contours of different patients.

In another embodiment, this disclosure discloses a frame assembly for a ventilator to deliver gas, configured to deliver positive pressure breathing gas from a flow generator to a patient's airway for the treatment of sleep breathing disorders, the frame assembly for a ventilator to deliver gas including at least some of the following elements or features.

A frame has a first interface and two second interfaces, with the first interface set on the forehead of the patient to receive positive pressure breathing gas and the second interfaces near both nasal sides of the patient.

The frame has a symmetrical hollow tube, connectable to the first interface positioned at the center of the frame and to the second interfaces on each nasal side of the patient, to deliver positive pressure breathing gas from the first interface to the second interfaces. The hollow tube has a front wall, a back wall, an inner edge and an outer edge formed at the junction of the front wall and the back wall.

Wing elements are configured to connect to a headgear to secure the frame on the patient's face, having a first wing element on the outer edge of the hollow tube near the first interface, and a second wing element on the outer edge of the hollow tube near the second interface.

A rigid interface is configured to detachably connect to a patient interface cushion, which is set at the ends of the second interfaces of the frame, forming an undetachable connection with the second interface.

In one embodiment, the frame assembly can include a quick-release component to connect to the headgear and the second wing element, situated at the end of the second wing element away from the hollow tube, forming a detachable connection with the second wing element.

In one embodiment, the rigid interface is connectable to the second interface through co-molding or welding.

In one embodiment, the rigid interface has at least a protrusion to connect to the patient interface cushion.

In another embodiment, this disclosure discloses a frame assembly for a ventilator to deliver gas, configured to deliver positive pressure breathing gas from a flow generator to a patient's airway for the treatment of sleep breathing disorders, the frame assembly for a ventilator to deliver gas including at least some of the following elements or features.

A frame made of continuous hollow elastomer has a first interface to receive positive pressure breathing gas, a second interface near the patient's nasal side, and a hollow tube extending between the patient's eyes and ears to connect the first interface and the second interface.

Wing elements, configured to connect to a headgear to secure the frame on the patient's face, have a first wing element on a hollow tube near the first interface, and the second wing elements on the hollow tube near the second interface.

There is at least one first wing element, extending from the hollow tube towards the area above the ears, with at least one opening to connect to a headgear, providing the frame with a pulling force towards the back part of the head when worn.

There are at least two second wing elements extending from the hollow tube towards the area below the ears to connect to the headgear, providing the frame with a pulling force towards the back part of the head when worn, which pulls a patient interface cushion nearer the patient's airway.

The hollow tube includes a support portion on an inner wall corresponding to the first interface, which is configured to prevent the gas delivery device from bottoming out and sealing off a pressurized airflow when connected to the first interface.

In one embodiment, the first interface has an annular wall that extends into the interior cavity of the hollow tube, strengthening the connection and ensuring an effective seal with the gas delivery device.

In one embodiment, the hollow tube has a front wall away from the patient's face and a back wall near the patient's face, and the first interface penetrates through the front wall of the hollow tube.

In one embodiment, the hollow tube extends from a first nasal side of the patient, ascends towards a first temporal region, then extends to a second temporal region and reaches a second nasal side, forming a contour that at least partially encircles the patient's eyes and nose.

In one embodiment, the support portion is a strip-like protrusion formed on the inner wall of the hollow tube, and the length of the support portion exceeds the distance between the intersecting points at which the first interface meets the straight line extending from the support portion in a lengthwise direction.

In another embodiment, this disclosure discloses a frame assembly for a ventilator to deliver gas, configured to deliver positive pressure breathing gas from a flow generator to a patient's airway for the treatment of sleep breathing disorders, the frame assembly for a ventilator to deliver gas including at least some of the following elements or features.

A frame has a first interface and two second interfaces, with the first interface being configured to receive positive pressure breathing gas and the second interfaces near the patient's nasal sides.

The frame has a symmetrical hollow tube, connectable to the first interface positioned at the center of the frame and to the second interfaces on each nasal side of the patient, to deliver positive pressure breathing gas from the first interface to the second interfaces. The hollow tube has a front wall, a back wall, an inner edge and an outer edge formed at the junction of the front wall and the back wall.

An automatic adjustment mechanism, located on the hollow tube near the first interface of the frame without extending beyond the patient's zygomatic bones, is used to automatically adapt the length or width of the hollow tube to accommodate the facial contours of different patients.

Wing elements are configured to connect to a headgear to secure the frame on the patient's face, with a first wing element extending towards the area above the ears on the outer edge of the hollow tube near the first interface, and a second wing element extending towards the area below the ears on the outer edge of the hollow tube near the second interface. The second wing element has at least one opening to connect to a quick-release component or a headgear.

The hollow tube extends from a first nasal side of the patient, ascends towards a first temporal region, then extends to a second temporal region and to a second nasal side, forming a contour that at least partially encircles the patient's eyes and nose.

In one embodiment, the automatic adjustment mechanism can be folded walls made from elastomeric material with multiple concave sections and convex sections.

In one embodiment, the front wall of the hollow tube is arc-shaped, while the back wall is of a flat-plate type.

In one embodiment, the quick-release component has the form of a magnetic clasp or a clip.

In one embodiment, one end of the hollow tube near the first interface is larger than the end near the second interface.

In another embodiment, this disclosure discloses a frame assembly for a ventilator to deliver gas, configured to deliver positive pressure breathing gas from a flow generator to a patient's airway for the treatment of sleep breathing disorders, the frame assembly for a ventilator to deliver gas including at least some of the following elements or features.

A frame, made of continuous hollow elastomer, has a first interface on a forehead of the patient to receive positive pressure breathing gas, a second interface near a nasal side of the patient, and a hollow tube extending between the patient's eye and ear on each side to connect the first interface and the second interface.

An automatic adjustment mechanism, located on the hollow tube near the first interface of the frame, is used to automatically adapt the length or width of the hollow tube to accommodate the facial contours of different patients.

A rigid interface, made from a material more rigid than the material of the frame, is set at one end of the second interface of the frame, forming an undetachable connection with the second interface.

Wing elements are configured to connect to a headgear to secure the frame on the patient's face, with a first wing element on an outer edge of the hollow tube near the first interface, and a second wing element on the outer edge of the hollow tube near the second interface.

The hollow tube extends from a first nasal side of the patient, ascends towards a first temporal region, further rises to the forehead, then extends to a second temporal region and reaches a second nasal side, forming a contour that at least partially encircles the patient's eyes and nose.

In one embodiment, the automatic adjustment mechanism is integrally formed with the hollow tube and is made of silicone with a hardness of at or between 30 A to 70 A on a Shore scale.

In one embodiment, the frame assembly can include a connecting component, which has a first port to connect to the rigid interface and a second port to connect to a patient interface cushion, forming a detachable connection with both the rigid interface and the patient interface cushion.

In one embodiment, the first port of the connecting component corresponds to the rigid interface in shape and size, while the second port of the connecting component corresponds to the patient interface cushion in shape and size.

The benefits of the frame assembly for a ventilator to deliver gas provided by this disclosure can at least include:

1) The frame assembly of this disclosure is more stable than existing frames which have tubes with the air inlet set atop the patient's head. Existing tubular frames are susceptible to dislocation, prompted by their inherent weight coupled with the traction from the gas delivery device, particularly when the patient assumes a supine posture. This instability often results in the inadvertent displacement of the patient interface cushion, leading to gas leakage. In contrast, the frame assembly provided by this disclosure envelops the patient's face, placing the air inlet at the forehead. This orientation capitalizes on the supportive force exerted by the forehead in a supine position, counteracting the gravitational pull of the frame, which prevents the frame from descending and disrupting the positioning of the patient interface cushion, thereby avoiding gas leakage. Moreover, the gas interface of the frame set directly on the patient's face allows patients to discern the location of the gas interface with a mirror, which is an improvement over traditional designs that situate the gas interface on the headgear since this design simplifies the installation of the elbow or other gas delivery devices. Besides, the frame has an automatic adjustment mechanism that allows it to automatically adapt to the patient's facial shape when worn in response to the dual effects of gravity and the pulling force, ensuring a better fit that maintains intimate contact with the patient's facial contours.

2) The frame assembly of this disclosure has at least three headgear connection points, a design choice that improves its stability and airtightness compared to existing tubular frames with two connection points. Existing frame designs, which commonly have only two pulling forces exerted on the frame above the ears towards the back part of the head, inadequately counteract the frame's tendency to slide downward. When patients lie supine, the backward pull of the headgear on the frame makes it easier to pull the frame off the top of the head. Moreover, due to the absence of additional pulling forces surrounding the patient interface cushion, the patient interface cushion can easily shift away from the patient's airway, particularly when the patient is lying on her or his side. In contrast, the frame assembly presented herein has at least three pulling force points. One of the pulling forces comes from exerting forces on the upper part of the frame towards the upper and back parts of the head to combat gravitational pull so that the frame does not slip, ensuring the upper part of the frame fits against the facial contours of patients. Additionally, two pulling force points are applied to the frame near the nasal sides, pulling towards the back part of the head. This helps secure a snugger fit against the face and, indirectly, pulling the patient interface cushion into closer proximity with the nose. With three connection points for the headgear to encapsulate the head more securely, the nocturnal movements or variations in facial muscles exert minimal disruption to the stability of the frame assembly and the positioning of the patient interface cushion. The headgear has an elastic securing device, stabilizing the breathing tube on the patient's head, further bolstering the overall stability and dependability of the therapeutic assembly. The placement of the gas delivery device on the head, secured firmly with the headgear, eliminates concerns of tube detachment or entanglement during sleep. For added convenience during disassembly, the frame assembly incorporates a quick-release component which enables patients to swiftly separate the frame from the headgear, avoiding the need to repeatedly adjust the length of the headgear.

3) The frame assembly of this disclosure has a smoother airflow, which is an improvement over existing designs where the frame extends from the patient's nasal side to the top of the head. Existing frames, although configured to bypass the zygomatic bone's apex, unavoidably cross over the lateral bones of the head. When the patient is lying on her or his side, the tube on one side is easily pressed, disrupting airflow to the patient's airway, and diminishing sleep quality. Conversely, the frame of this disclosure is set at the front of the patient's face, avoiding protruding skeletal structures, such as the zygomatic bones and the forehead. As a patient or user lies on her or his side, the patient's or user's cheeks, which are the softer portion of the face, contact the frame, which is less likely to press the tube and helps maintain smooth airflow to the maximum extent throughout the therapeutic session.

4) The frame assembly of this disclosure incorporates connecting components. With the replacement of connecting components, the connection of a single frame with different types of patient interface cushions can be achieved, which allows patients to select cushions that best meet their needs. For example, patient interface cushions with a male connector can be paired with connecting components featuring a female counterpart, and vice versa, patient interface cushions with a female connector can also be paired with connecting components with a male connector. This compatibility achieves a modular function without having to replace the entire frame or patient interface cushion and it requires merely the substitution of a minor component, providing better choices for both manufacturers and patients. For manufacturers, they are no longer confined to interfaces that connect with the frame when designing patient interface cushions, and have more space for pioneering designs. Patients, on the other hand, can opt for patient interface cushions of different types, structures, and functionalities. Furthermore, this approach of interchangeable connections between multiple frames and patient interface cushions presents an environmental upside. Separately designed and replaceable connecting components bring reduced consumption of raw materials, effectively conserving existing resources for sustainable energy use, minimizing production waste, and reducing carbon emissions and climate change.

5) In comparison to current non-tubular frames that create a seal around the patient's airway, the frame assembly of this disclosure offers an expanded area of contact with the face, made from elastomer, which helps distribute the force applied by the headgear. This results in reduced pressure on the face, preventing squeezing of the patient's face. Furthermore, unlike existing methods, this design locates the gas interface away from the patient's face, mitigating disruptions from exhaust airflow and diminishing noise sensitivity, thereby fostering a more serene sleeping experience for the patient.

DETAILED DESCRIPTION

Figure 1:
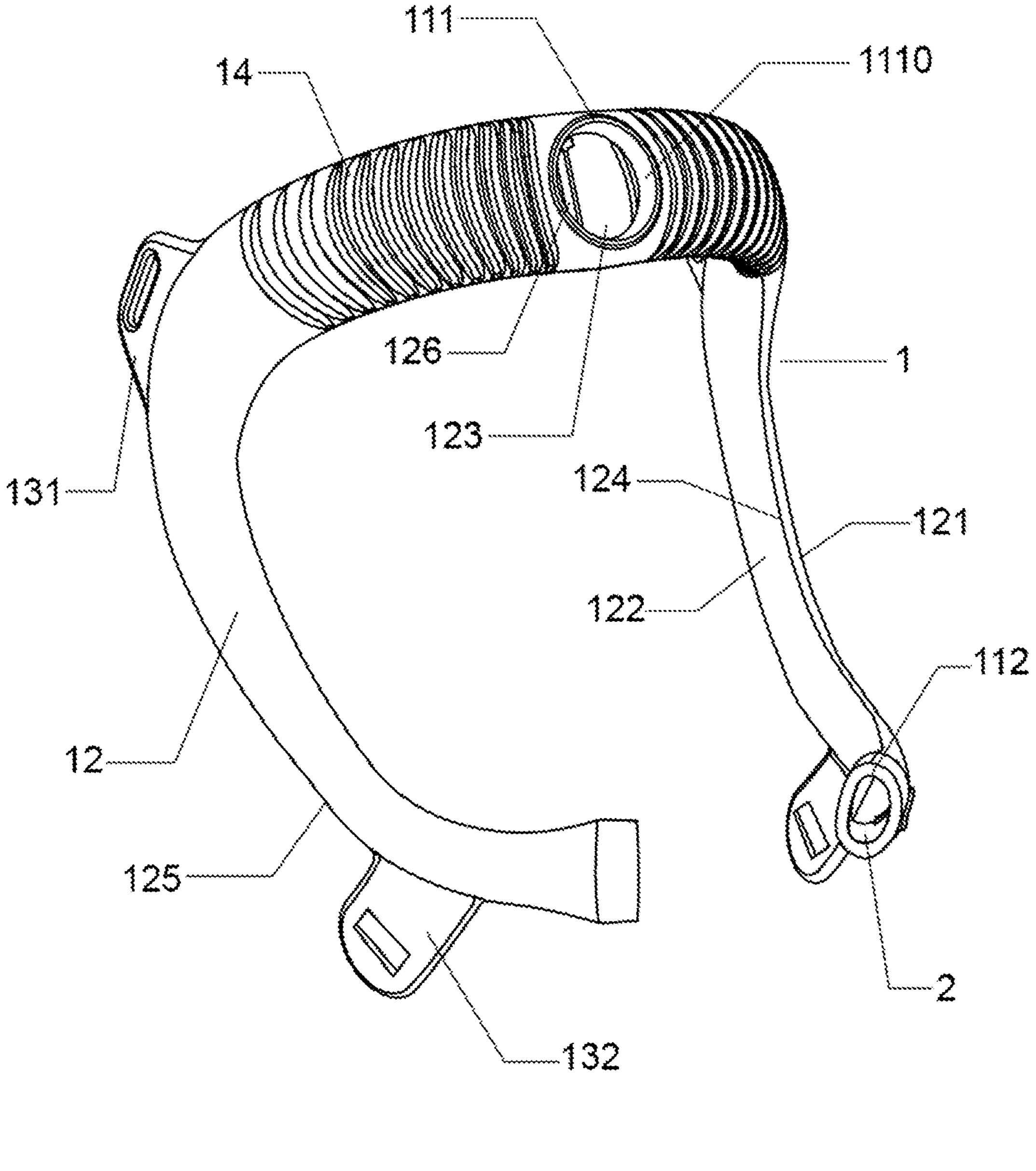
FIG. 1 is a three-dimensional schematic diagram of the frame assembly in accordance with an example embodiment.

To clarify the objectives, characteristics, and merits of this disclosure, provided herein is a comprehensive description of specific embodiments, supplemented by accompanying diagrams. This explanation delves into precise details to ensure a robust comprehension of this disclosure. It is noteworthy, however, that the scope of the disclosure accommodates various implementations beyond those explicitly outlined herein. Professionals in the relevant field can introduce analogous alterations without deviating from the fundamental principles of the disclosure. As such, the disclosure should not be construed narrowly and is not restricted to the precise embodiments disclosed in the subsequent description.

The air inlet of existing tubular frames is positioned on the top of the head and has only two connection points for the headgear. Such a design tends to cause the frame to shift or fall off during sleep, which compromises the sealing of the patient interface cushion. Additionally, when lying on one's side, it is easy to compress one side of the tube, causing it to close and affect airflow. Traditional frames also exert too much pressure on the face, leading to red marks and pressure sores. To address these issues, this disclosure provides a frame with a symmetrical hollow tube. Uniquely, the air inlet is located at the patient's forehead and extends and wraps around from the front side of the patient's head. This positioning alleviates the issue of the frame being pressed by the skull when the patient is lying on her or his side. To further enhance stability and comfort, the disclosure employs no less than three connection points for the headgear, ensuring a firm yet comfortable fit of the frame, thereby improving the patient's experience.

To elucidate further, references are made to FIG. 1 to FIG. 9. The frame assembly of this disclosure includes a frame 1, wing elements, an automatic adjustment mechanism 14, and a rigid interface 2. The frame 1 is made of continuous hollow elastomer, granting it specific elasticity and deformability, which can be made from one or several types among silicone, rubber, latex, and TPE. The hardness range is at or between 30 A to 70 A on the Shore scale, with a preferable scope at or between 40 A to 60 A. Preferably, the frame 1 is made from silicone within a hardness range of at or between 30 A to 70 A. The frame 1 has a first interface 111 to accommodate positive breathing gas, and a second interface 112 positioned near the patient's nasal side. The first interface 111, typically circular in design, requires a diameter greater than 15 mm to guarantee a sufficient influx of gas into the frame 1, crucial for therapeutic effectiveness. The first interface 111 resides centrally on the frame 1, with its diameter not exceeding 35 mm to avoid problems such as undue heaviness, impeded vision, or an unstable connection with the gas delivery device 8. While the standard form is circular, the first interface 111 could adopt other shapes, such as square, oval, or triangular. The first interface 111 is used to connect to the gas delivery device 8 and has an annular wall 1110 extending into the cavity of the hollow tube 12. This configuration strengthens the connection and ensures airtight interfacing with the gas delivery device 8. The second interface 112 is located nearer the nose. Given the more pronounced facial contours and reduced space in this region compared to the broader area of the forehead, the perimeter of the second interface 112 is smaller than that of the first interface 111.

Figure 4:
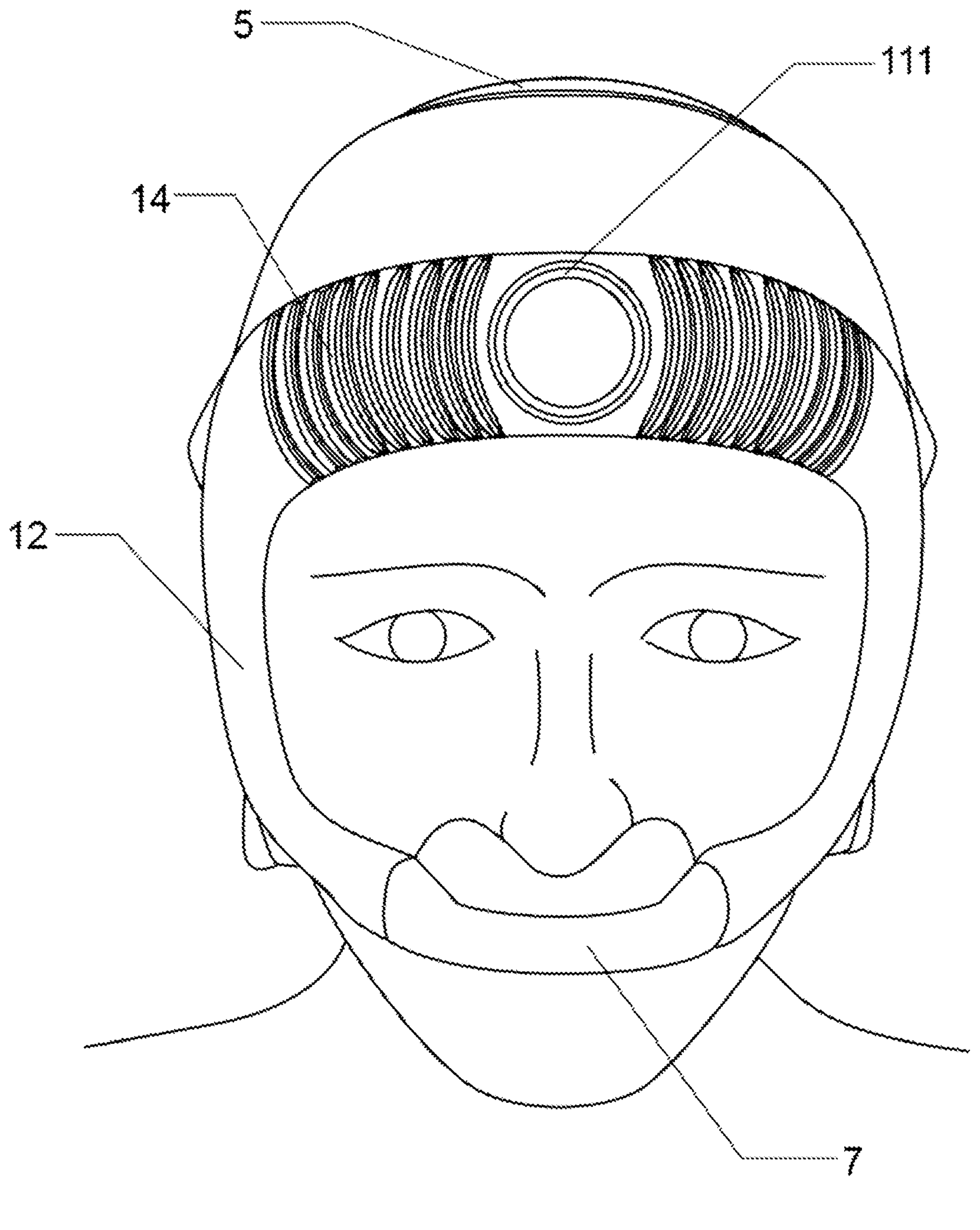
FIG. 4 is a front view of the frame assembly in its worn state in accordance with an example embodiment.
Figure 8:
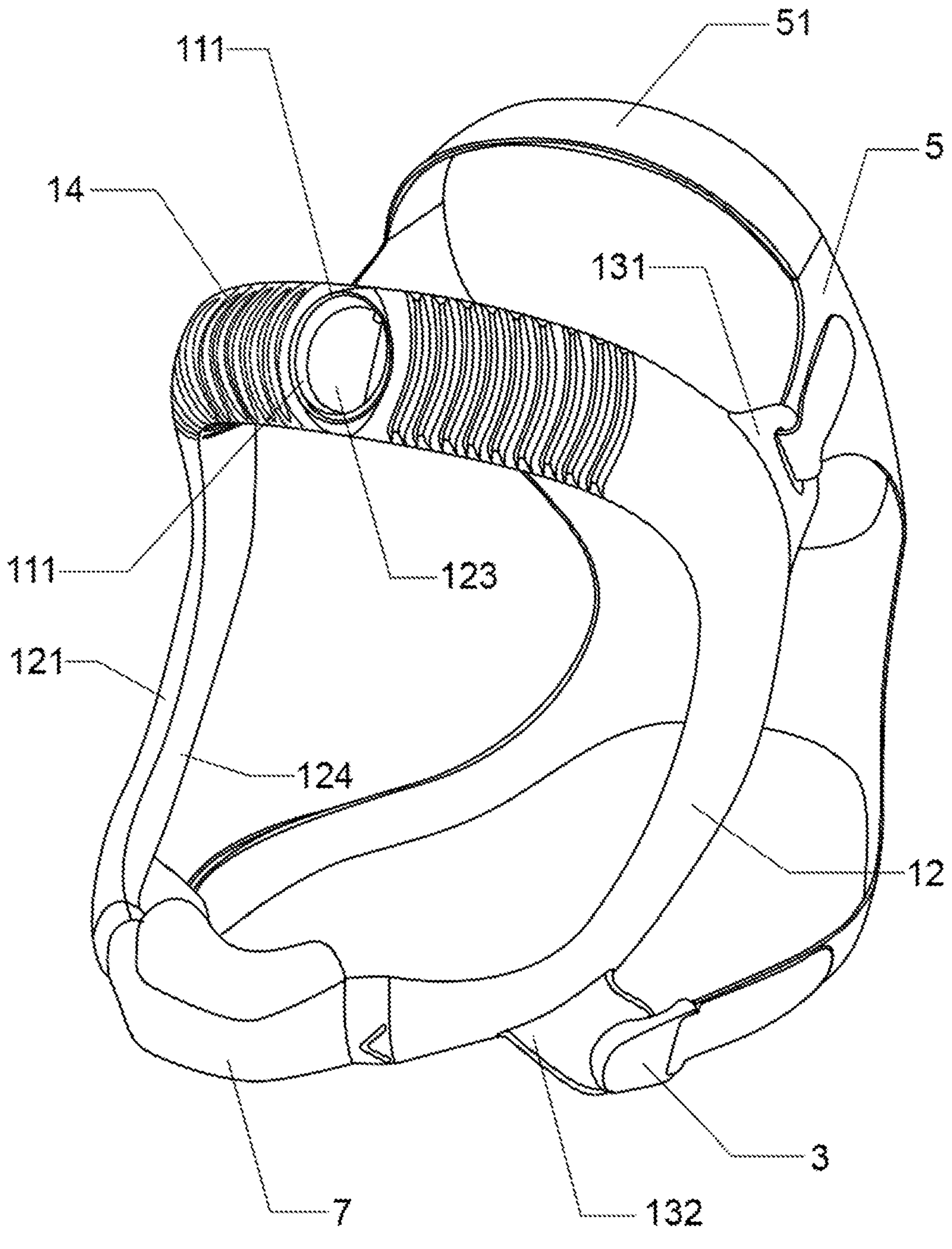
FIG. 8 is a schematic diagram illustrating the connection of the frame assembly with the headgear and the patient interface cushion in accordance with an example embodiment.
Figure 9:
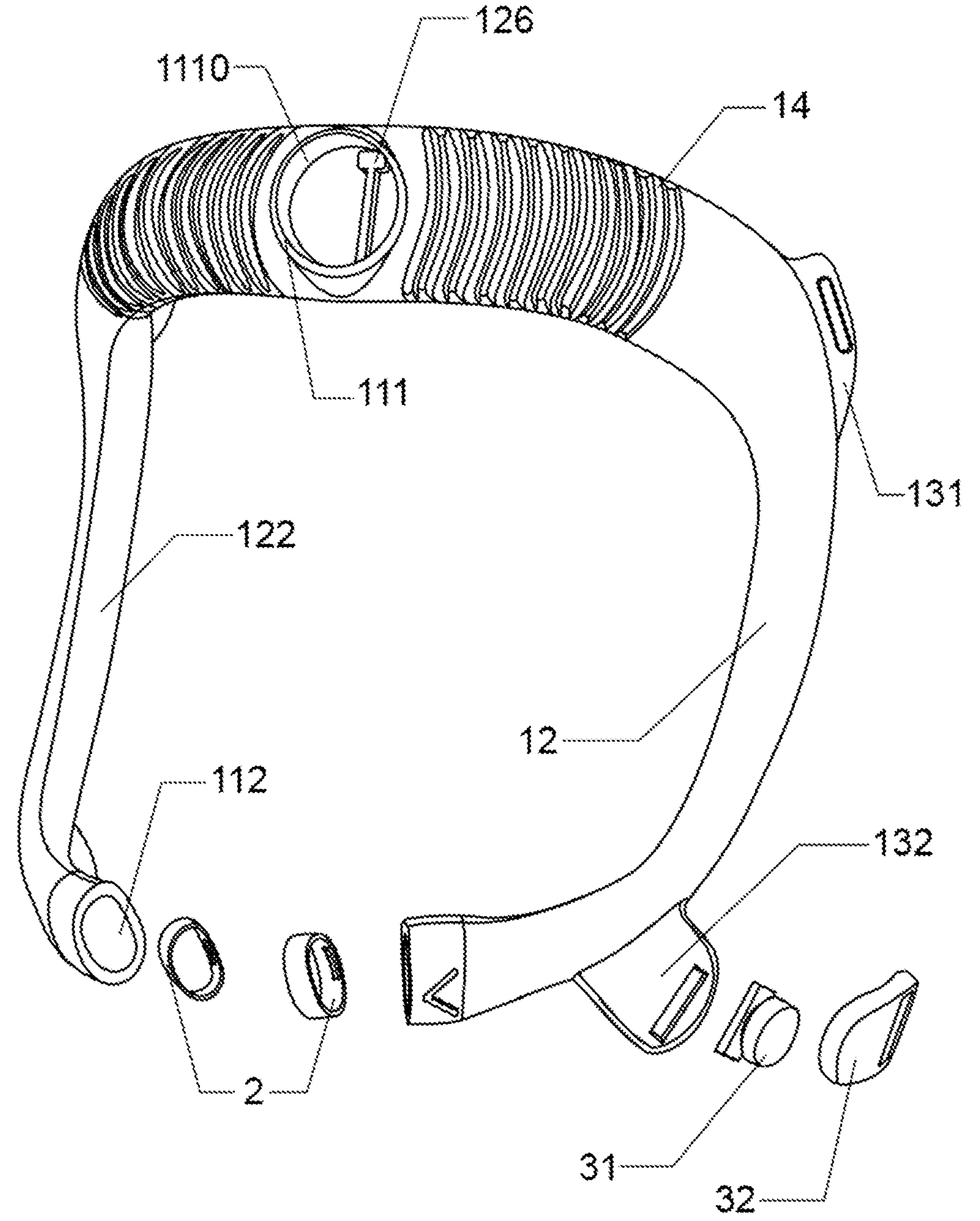
FIG. 9 is an exploded schematic diagram of the frame assembly and the quick-release component in accordance with an example embodiment.
Figure 20:
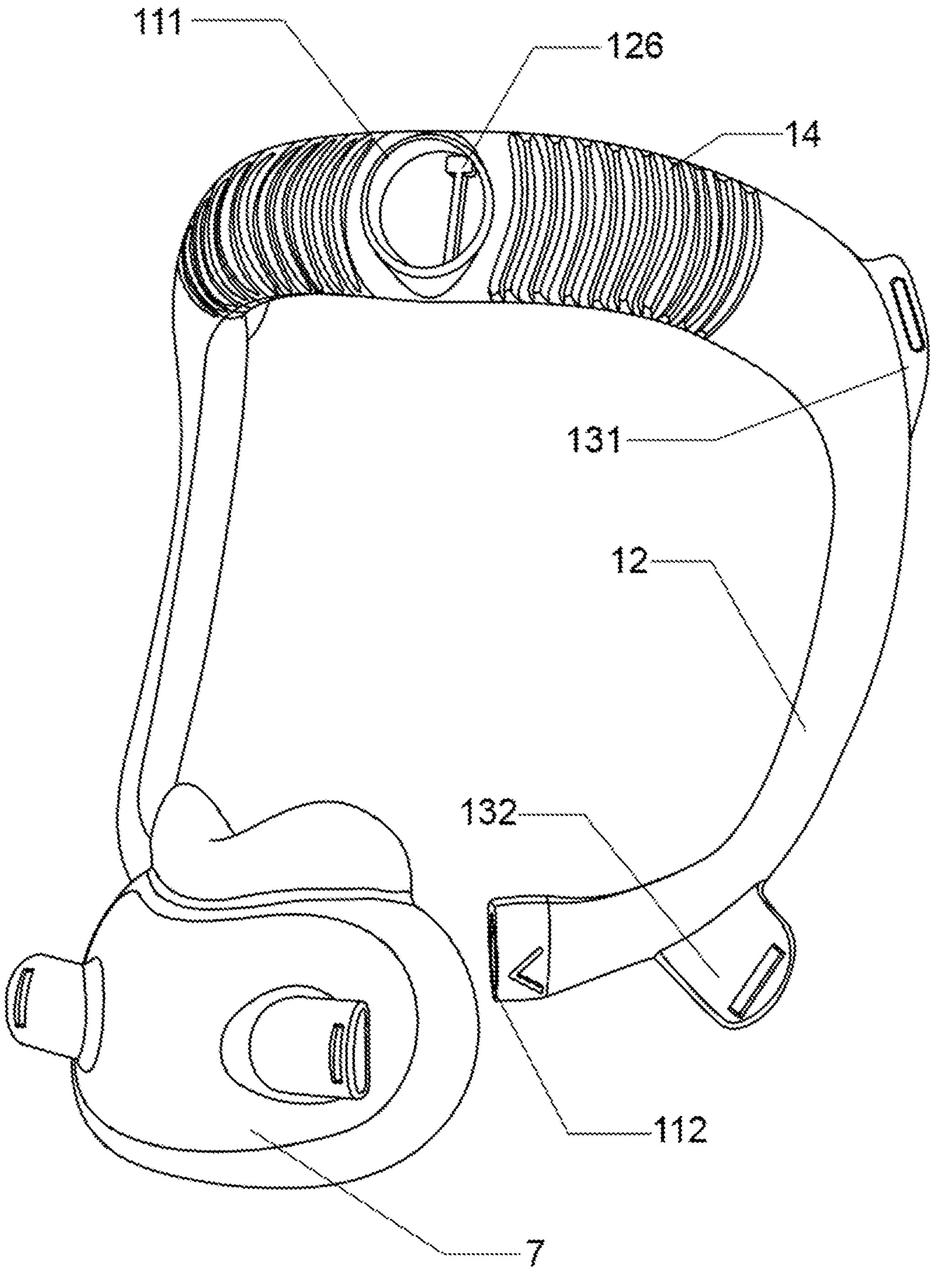
FIG. 20 is a schematic diagram illustrating the patient interface cushion of the oronasal mask type connected with the frame assembly in accordance with Embodiment 1.
Figure 21:
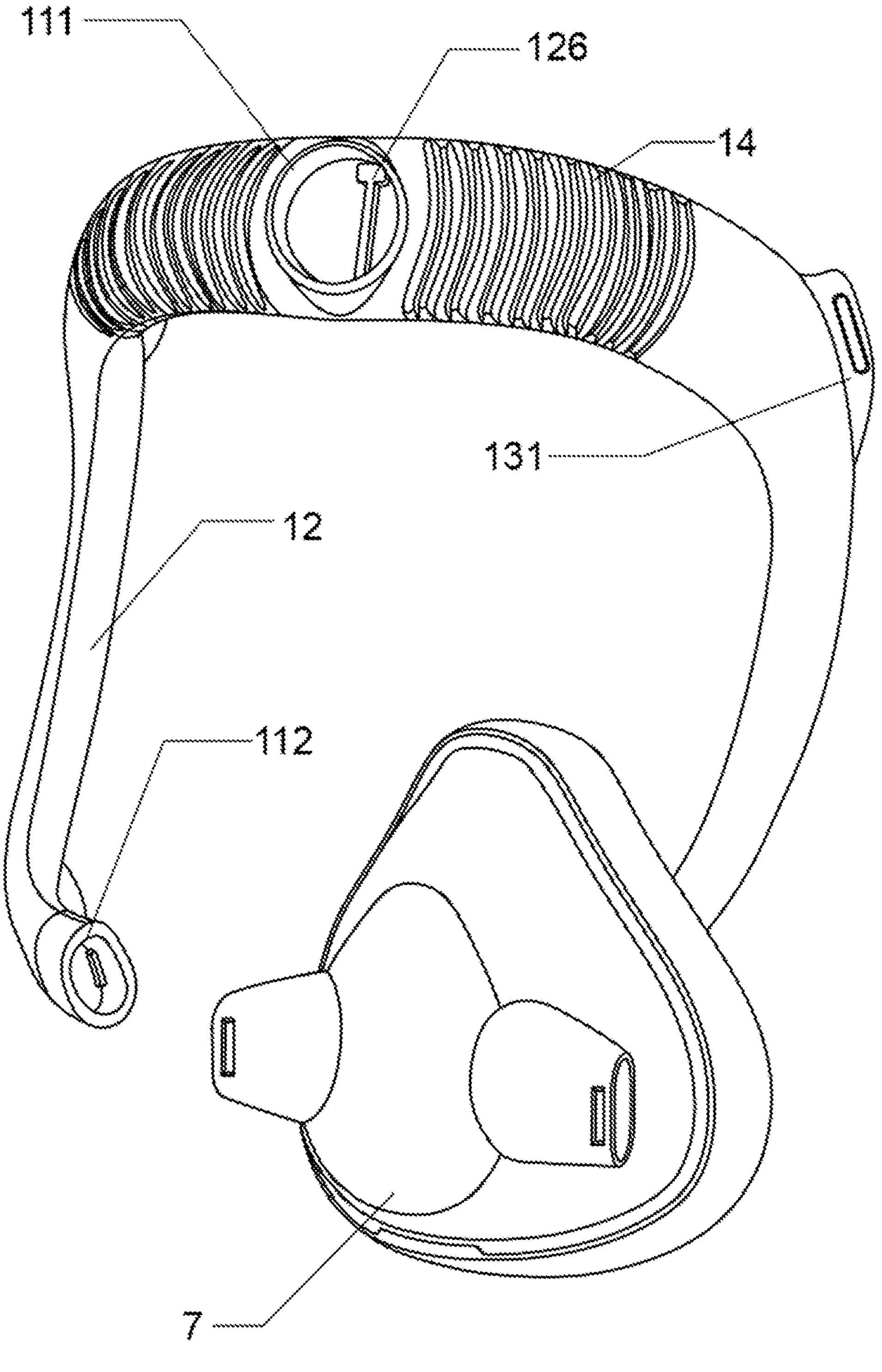
FIG. 21 is a schematic diagram showing the patient interface cushion of the full-face mask type connected with the frame assembly in accordance with Embodiment 1.

The frame 1 also incorporates a symmetrical hollow tube 12 which is connected to the first interface 111 at the center of the frame 1 and to two second interfaces 112 respectively situated near the patient's nasal sides. The hollow tube 12 is configured to deliver positive breathing gas from the first interface 111 to the second interface 112, which extends from the patient's first nasal side (left side) upward to the first temporal region (left side), then across to the second temporal region (right side), and downward to the second nasal side (right side), forming a contour that partially encircles the patient's eyes and nose. The hollow tube has a front wall 121 (away from the patient's face), a back wall 122 (nearer the patient's face), an inner edge 124 (nearer the patient's eyes during use) and an outer edge 125 formed at the juncture of the front wall 121 and the back wall 122. The first interface 111 penetrates the front wall 121 of the hollow tube 12 to connect with the gas delivery device 8, while the second interface 112 connects with the patient interface cushion 7, creating a continuous airflow circuit. The front wall 121 of the hollow tube 12 at the end of the second interface 112 can also include identifiers distinguishing left from right. The end of the hollow tube 12 near the first interface 111 is broader than the end near the second interface 112. It's important to note that the patient interface cushion 7 could be a nasal mask or a nasal pillow that encloses only the patient's nasal airway, as shown in FIG. 4 and FIG. 8, or the patient interface cushion 7 could be a full-face mask or an oronasal mask encompassing both the patient's nasal and oral airways, as depicted in FIG. 20 and FIG. 21.

Figure 13:
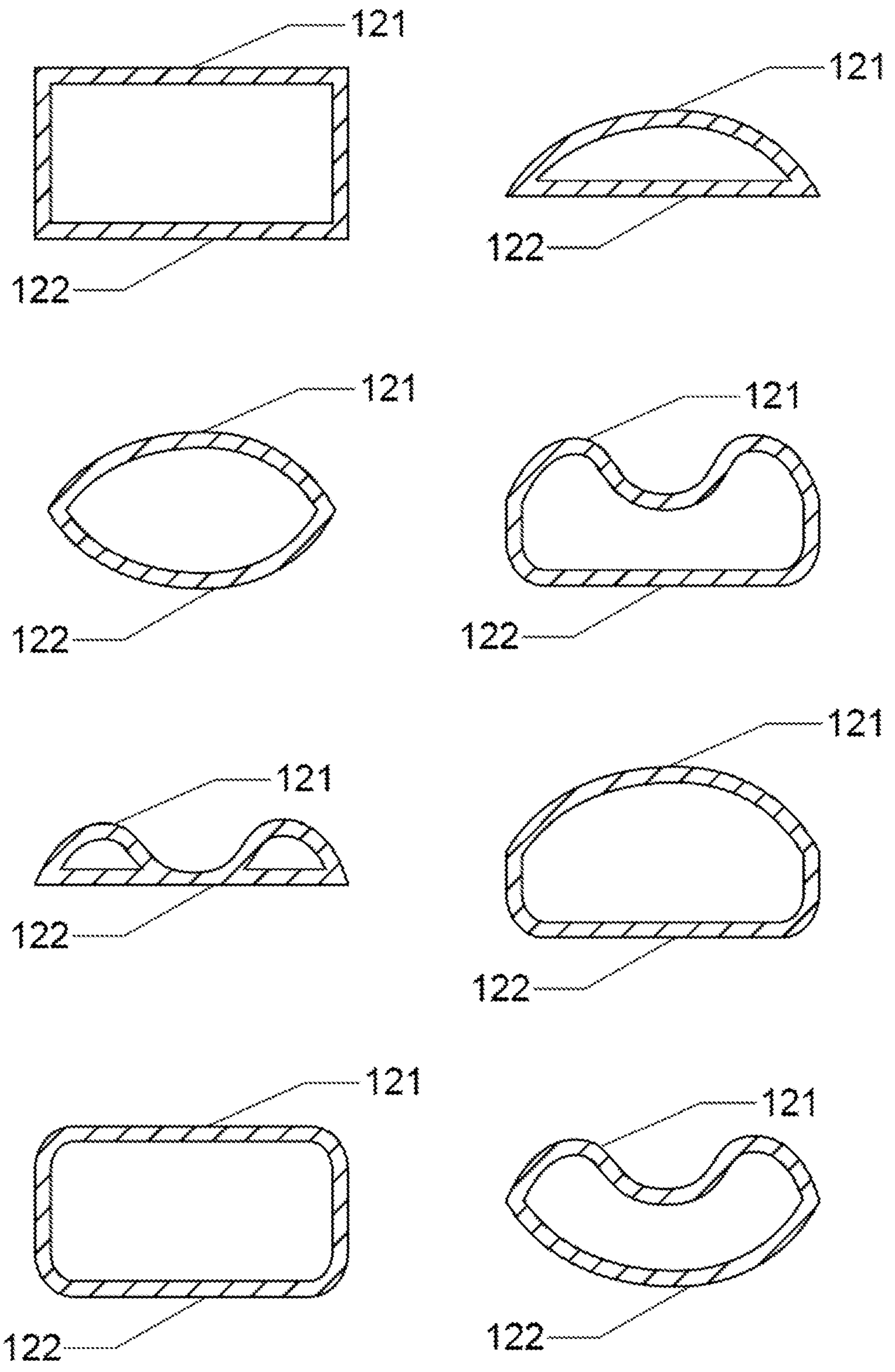
FIG. 13 is a cross-sectional schematic diagram of the hollow tube in accordance with multiple embodiments.

The front wall 121 and the back wall 122 of the hollow tube 12 can adopt various cross-sectional configurations, including forms such as square bracket, arc, wavy, or flat-plate profile, as depicted in FIG. 13. Generally, one portion of the back wall 122, which contours to the face, maintains a flat surface to optimize patient comfort. To safeguard the airflow of the frame 1, neither the front wall 121 nor the back wall 122 should be solely flat-plate. Various combinations are permissible, provided that the front wall 121 and the back wall 122 are not flat-plate simultaneously, such as both the front wall 121 and the back wall 122 being arced, or an arced front wall 121 and a flat-plate back wall 122, or a wavy front wall 121 coupled with a flat-plate back wall 122 (which prevents airflow obstruction due to the front wall 121 bottoming out under pressure). For aesthetic reasons, production needs, and user comfort, the edges of both the front wall 121 and the back wall 122 should be rounded. The thickness of the front wall 121 and the back wall 122 in the hollow tube 12 can be uniform or may be non-uniform. For example, a shell-like cross-sectional profile with a thinner inner edge 124 and a thicker outer edge 125 helps mitigate facial pressure. Alternatively, a design with thicker inner edge 124 and outer edge 125 and thinner front wall 121 and back wall 122, better supports the interior space of the hollow tube 12, preventing collapse.

Figure 12:
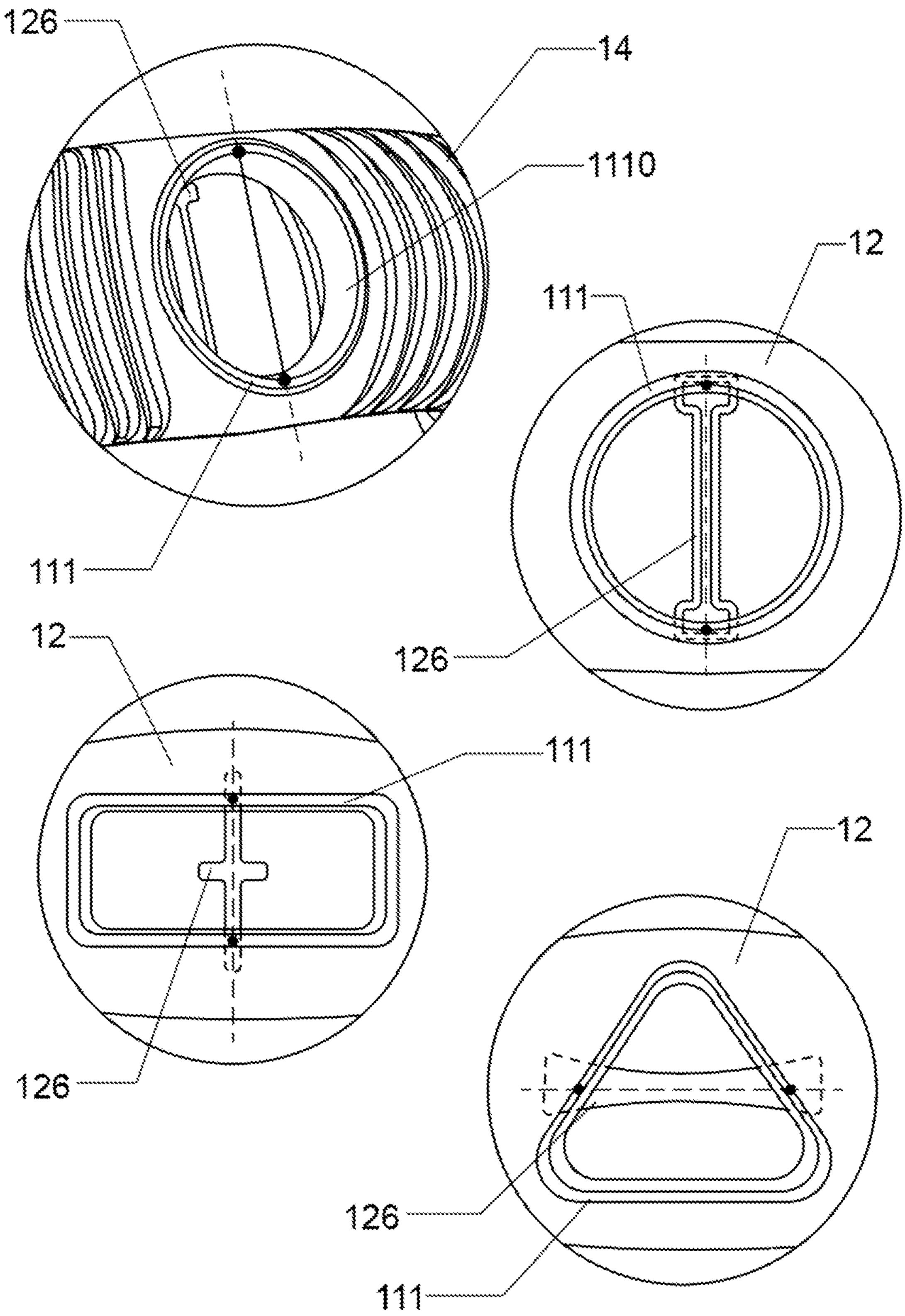
FIG. 12 is a schematic diagram of the first interface and the support portion in accordance with multiple embodiments.

The inner wall 123 of the hollow tube 12 near the first interface 111 incorporates a support portion 126 to prevent the gas delivery device 8 from bottoming out and obstructing the pressurized airflow upon connection with the first interface 111. The support portion 126 is structured as a strip-like protrusion from the inner wall 123 of the hollow tube 12, which ensures that the gas delivery device 8, influenced by gravity, maintains contact with the support portion 126, fostering a clearance that permits the free passage of airflow. To ensure that the support portion 126 functions properly, as shown in FIG. 12, regardless of the shape or orientation of the support portion 126, the support portion 126 should have a length surpassing the distance between the intersecting points at which the first interface 111 meets the straight line extending from the support portion 126 in a lengthwise direction. This design precludes the gas delivery device 8 from bottoming out. In addition to its primary role, the support portion 126 also has another function for production needs which fulfills a protective function during manufacturing, safeguarding against abrasions or perforations of the hollow tube 12. Furthermore, multiple support portions 126 can be placed along the inner wall 123 at various positions within the hollow tube 12 to prevent it from bottoming out when pressed as the user lies on her or his side.

The wing elements are provided to connect to the headgear 5, thereby securing frame 1 to the patient's face. The wing elements include the first wing element 131 on the hollow tube 12 near the first interface 111, and the second wing element 132 on the hollow tube 12 near the second interface 112. The first wing element 131 incorporates at least one opening to connect to the headgear 5, whereas the second wing element 132 has at least one opening, suitable for connecting to the quick-release component 3 or the headgear 5. The number of first wing elements 131 is adaptable, provided they effectively stabilize the frame 1, with at least one extending towards the area above the ear from the hollow tube 12. In instances where a single first wing element 131 is utilized, the first wing element is preferably placed at the outer edge 125 of the hollow tube 12 in alignment with the first interface 111. When worn, the first wing element 131 extends upward and backward over the head. In conjunction with the headgear 5, a pulling force is exerted on the frame 1 towards the upper and back parts of the head, preventing the frame 1 from falling off. In scenarios with two first wing elements 131, a symmetrical arrangement on either side of the first interface 111 is preferable, which aids in lifting the frame 1 and also contributes to preserving the frame 1's contour. When employing three first wing elements 131, they can be located at the center and on both sides of the first interface 111 for optimal support and stability.

Figure 5:
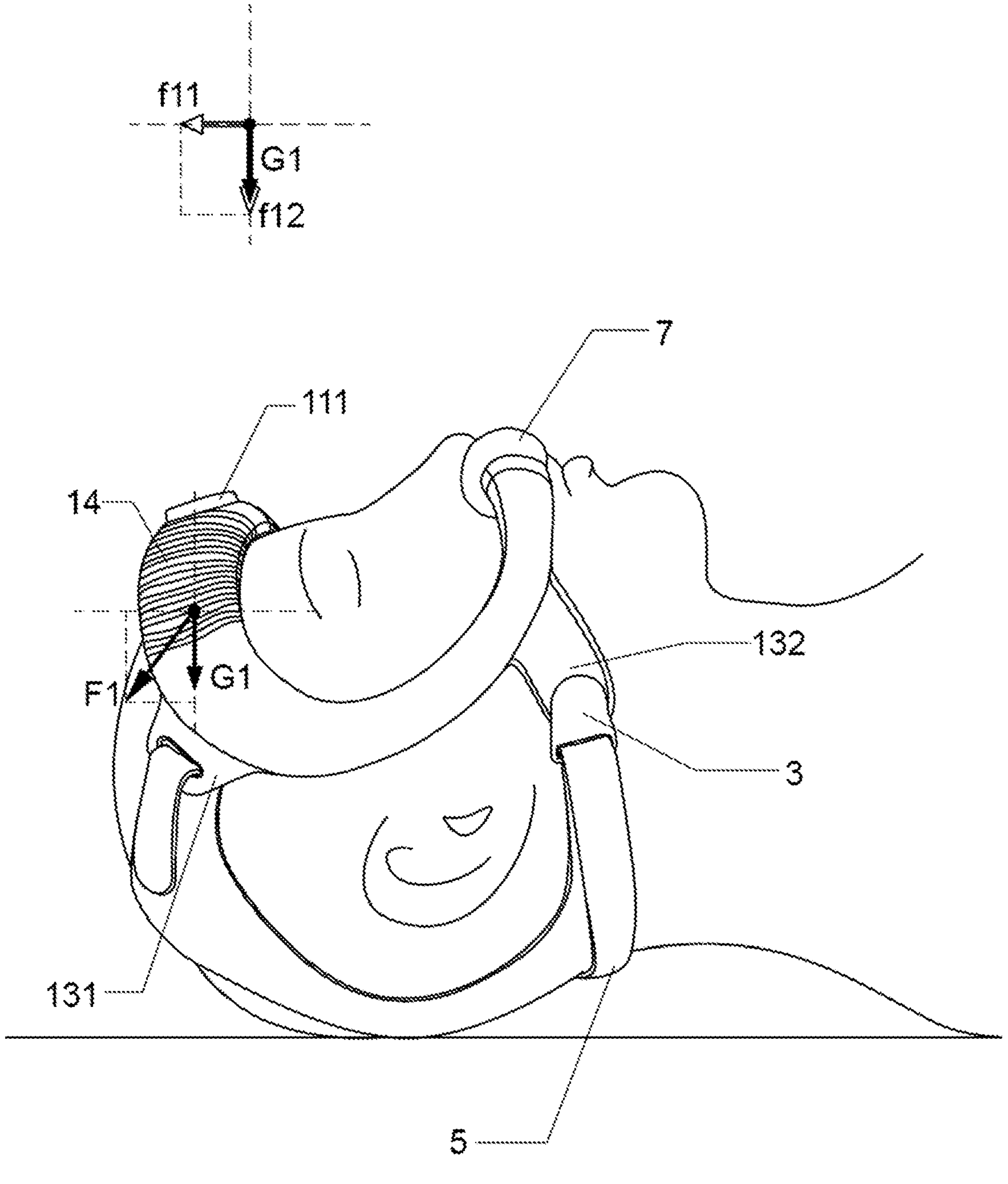
FIG. 5 is a schematic diagram of the frame assembly worn in a supine position in accordance with an example embodiment.
Figure 6:
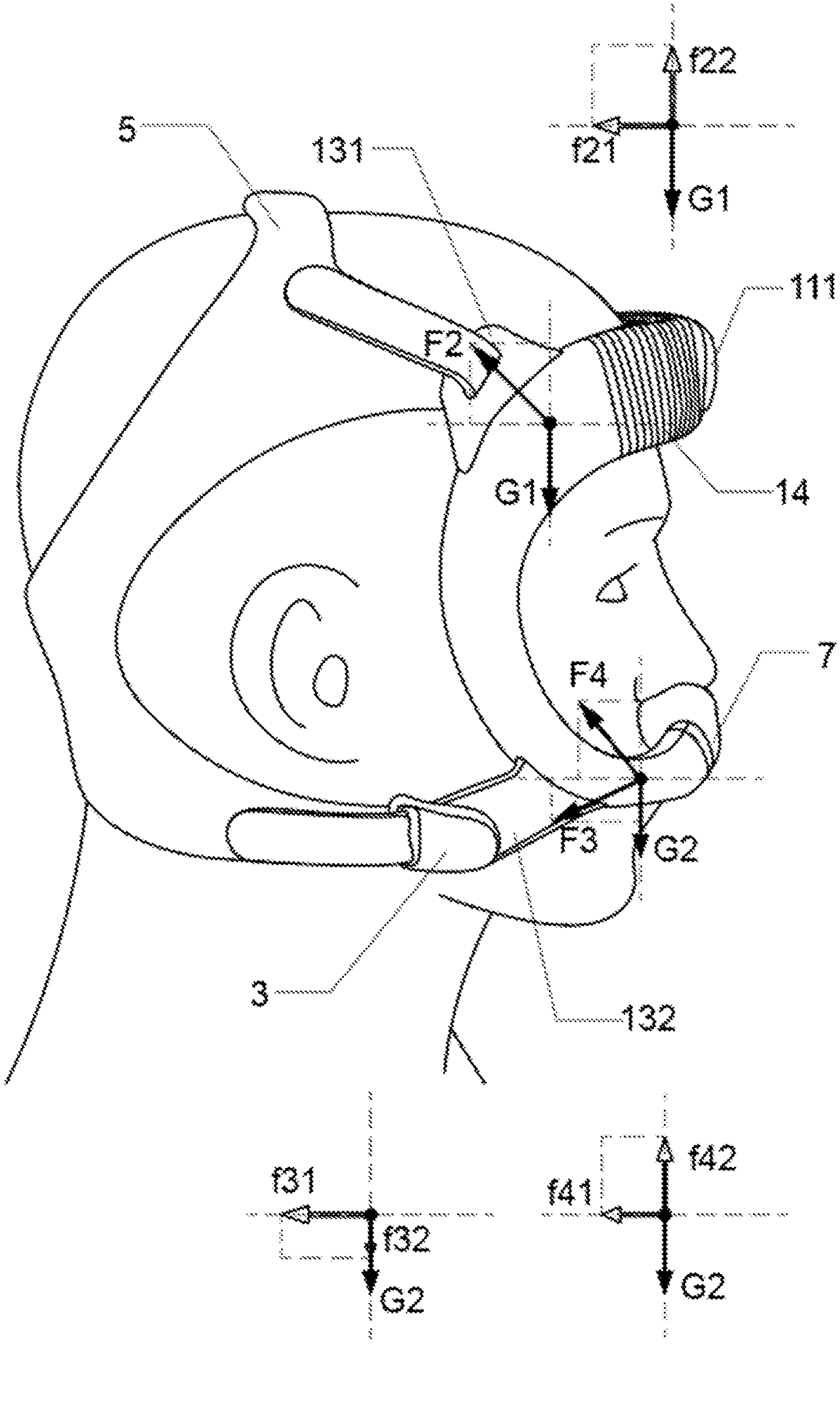
FIG. 6 is a left-side view of the frame assembly in its worn state in accordance with an example embodiment.

The first wing element 131 has at least one opening to connect to the headgear 5, providing the frame 1 with a pulling force towards the back part of the head when worn, thereby preventing the frame from slipping down due to gravity. There are at least two second wing elements 132, extending towards the area below the ears from the hollow tube 12 to connect to the headgear 5, which exerts a pulling force on the frame 1 towards the back part of the head when worn and draws the patient interface cushion 7 nearer the patient's airway. Furthermore, the extension of the second wing element 132 is concluded at the mandible, reducing the pressure on the face when the patient is lying on her or his side. The wing elements are to be soft enough to adapt to the unique contours of the patient's face, thus enhancing the overall comfort during use. The wing elements can be integrally formed with the hollow tube 12 during the molding process or be solidly joined with the hollow tube 12 using adhesive methods, forming an inseparable unit. There are alternative designs in which the wing elements are attached to the hollow tube 12 using external fixtures, such as strap buckles or ring buckles, allowing the adjustment of the wing elements' position as per the user's requirements. Preferably, the wing elements are configured to be integrally formed with of the frame 1. FIG. 5 is a schematic diagram of the frame assembly worn in a supine position while FIG. 6 is a left-side view of the frame assembly in its worn state. In these figures, G1 denotes the gravitational force on the frame 1, and F1 and F2 represent the forces exerted to the frame 1 by the headgear 5 through the first wing element 131. FIG. 5 reveals that, in the supine position, the first wing element 131 generates a force f11 towards the upper part of the head that anchors the frame 1 securely against the forehead while an upward supporting force on the frame 1 from the forehead (not depicted in the figure) helps maintain the frame 1 in a stable, fixed position. According to FIG. 6, it can be seen that when standing, the first wing element 131 has a force f21 applied to the frame 1 which extends towards the back part of the head and a force f22 exerted on the frame 1 which extends towards the upper part of the head. This draws the frame 1 intimately against the patient's face and partially counterbalances the frame 1's gravitational pull G1, preventing a downward slide toward the eyes. The patient interface cushion 7 is subject to its gravity G2. F3 is the force applied by the headgear 5 on the patient interface cushion 7 through the second wing element 132, and F4 is the force exerted by the frame 1 on the patient interface cushion 7. Forces f31 and f41 are directed towards the back part of the head, pressing the patient interface cushion 7 towards the patient's nose to ensure an effective seal. This setup avoids the patient interface cushion 7 being blown away from the patient's airway when receiving positive pressure gas. Additionally, an upward-directed force f42 partially counteracts the gravitational forces G2 and f32 on the patient interface cushion 7, lessening the pressure on the upper lip region. By optimizing the position and angle of the wing elements, they collaborate with the headgear 5 to exert a suitable pull on the frame 1. This design enables the frame 1 to be more stably secured to the patient's face, reducing the risk of air leakage from the patient interface cushion 7 and enhancing the seal's effectiveness.

Figure 14:
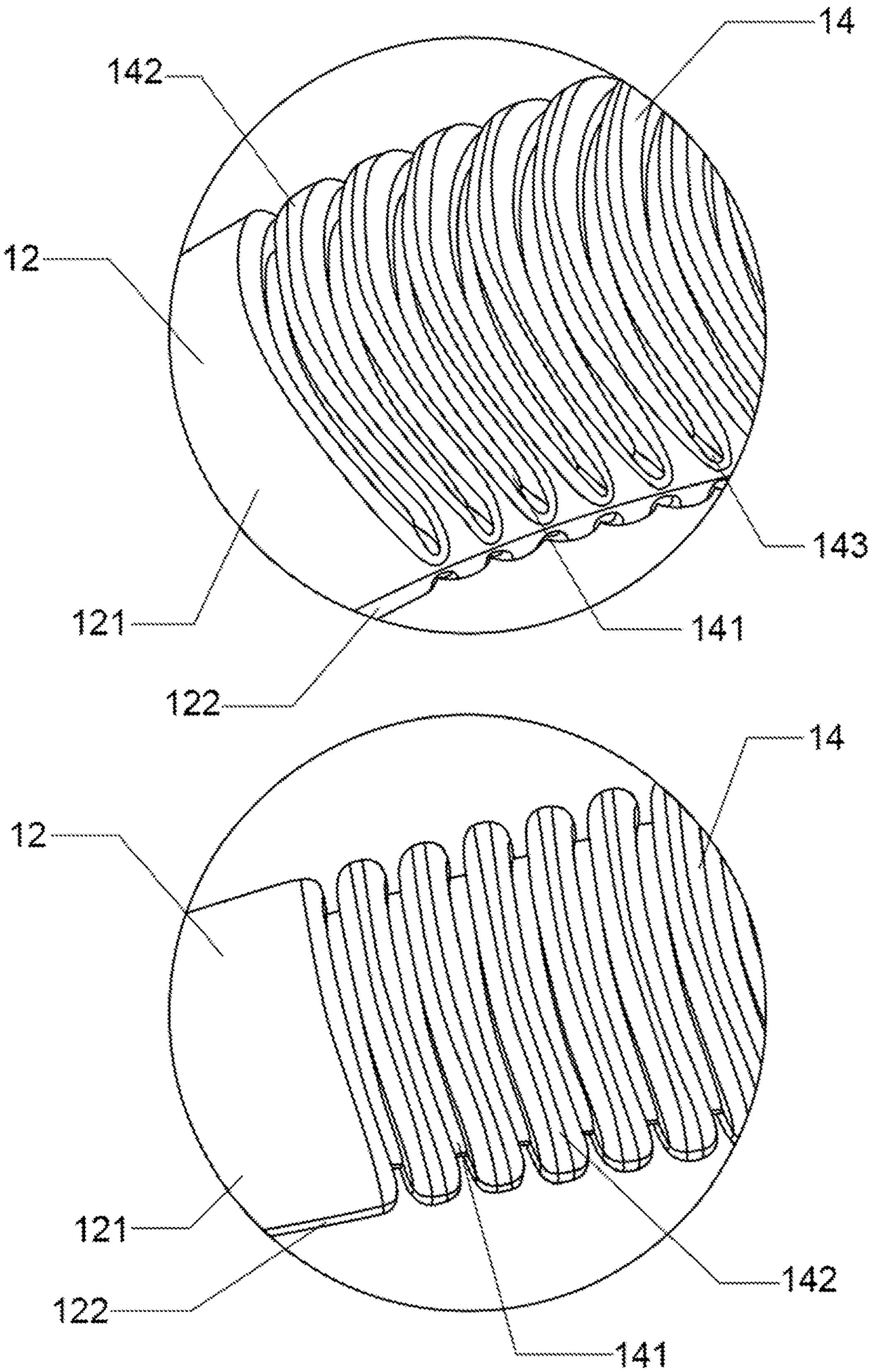
FIG. 14 is an enlarged schematic diagram of the automatic adjustment mechanism in accordance with multiple embodiments.

The frame assembly also includes an automatic adjustment mechanism 14, situated on the hollow tube 12 near the first interface 111. In at least one embodiment, the automatic adjustment mechanism is located on the hollow tube 12 near the first interface 111 without extending beyond the patient's zygomatic bones for automatically adapting (auto-deforming under gravity or a pulling force) the length or width of the hollow tube 12 to accommodate various patients' facial contours. The design of the automatic adjustment mechanism 14, not extending beyond the zygomatic bones, ensures the comfort of the frame assembly by being set at the forehead area which is less prone to being pressed during sleep, which prevents the concave and convex folded walls of the automatic adjustment mechanism 14 from pressing against the face. The automatic adjustment mechanism 14 has a design more susceptible to deformation compared to the hollow tube 12, composed of folded walls made from elastomeric material, featuring multiple concave sections 141 and convex sections 142, with a wall thickness not exceeding that of the hollow tube 12. When subjected to gravity or external forces, the automatic adjustment mechanism 14 adapts responsively, undergoing inward compression and outward expansion, vice versa, or experiencing simultaneous compression and expansion from both sides. In certain embodiments, illustrated in FIG. 14, measures are taken to counteract excessive ease of deformation in the automatic adjustment mechanism 14, which would make it difficult for the frame 1 to maintain its shape while being worn. One approach to preserving the shape of the frame 1 involves enhancing the automatic adjustment mechanism 14's rigidity. Furthermore, connecting walls 143 are introduced at the junctures corresponding to the inner edge 124 and the outer edge 125 of the hollow tube 12 within the automatic adjustment mechanism 14. These connecting walls 143 bridge the concave segments 141 among several folded walls, curbing excessive deformation differences between the interior side and the exterior side of the automatic adjustment mechanism 14, thereby constraining the extent of deformation within the automatic adjustment mechanism 14. This reinforcement ensures a balance between adaptability and stability, crucial for user comfort and device efficacy. The automatic adjustment mechanism 14 has two sides with one side having a sealed connection with the first interface 111, and the opposite side forming an airtight linkage with the hollow tube 12. Furthermore, the automatic adjustment mechanism 14 is integrally formed with the hollow tube 12, consisting of silicone with a hardness of at or between 30 A to 70 A on the Shore scale. In another embodiment, the automatic adjustment mechanism 14 is made inseparable from the hollow tube 12 through post-processing. In yet another embodiment, the automatic adjustment mechanism 14 is detachably connectable to the hollow tube 12.

The rigid interface 2, made from materials more rigid than materials of the frame 1, such as polycarbonate, polyamide, acrylonitrile butadiene styrene, polyvinyl chloride, or polyethylene, is positioned at the end of the second interface 112 of the frame 1, forming an undetachable connection with the second interface 112. The rigid interface 2 can be connected with the second interface 112 through various methods including co-molding, molding, ultrasonic welding, adhesives, welding, or mechanical fasteners, with a preference for either co-molding or welding. The rigid interface 2, configured to either be completely enveloped within or extend beyond the second interface 112, incorporates at least one protrusion or groove, facilitating a detachable connection with the patient interface cushion 7. The design of the rigid interface 2 should have a compact volume to prevent exerting undue pressure on the patient's nasal sides. In certain embodiments, the frame assembly may forgo the inclusion of a rigid interface 2, establishing a connection with the patient interface cushion 7 through the second interface 112 via a friction or snap fit (where the patient interface cushion 7 is smaller than the second interface 112 for snapping into place within the second interface 112). In another embodiment, there's flexibility to incorporate the rigid interface 2 either at the openings in the wing elements or near the first interface 111. Positioning the rigid interface 2 at the openings of wing elements contributes to maintaining their shape, avoiding deformation of the openings of wing elements during the application of a pulling force by the headgear 5.

Figure 11:
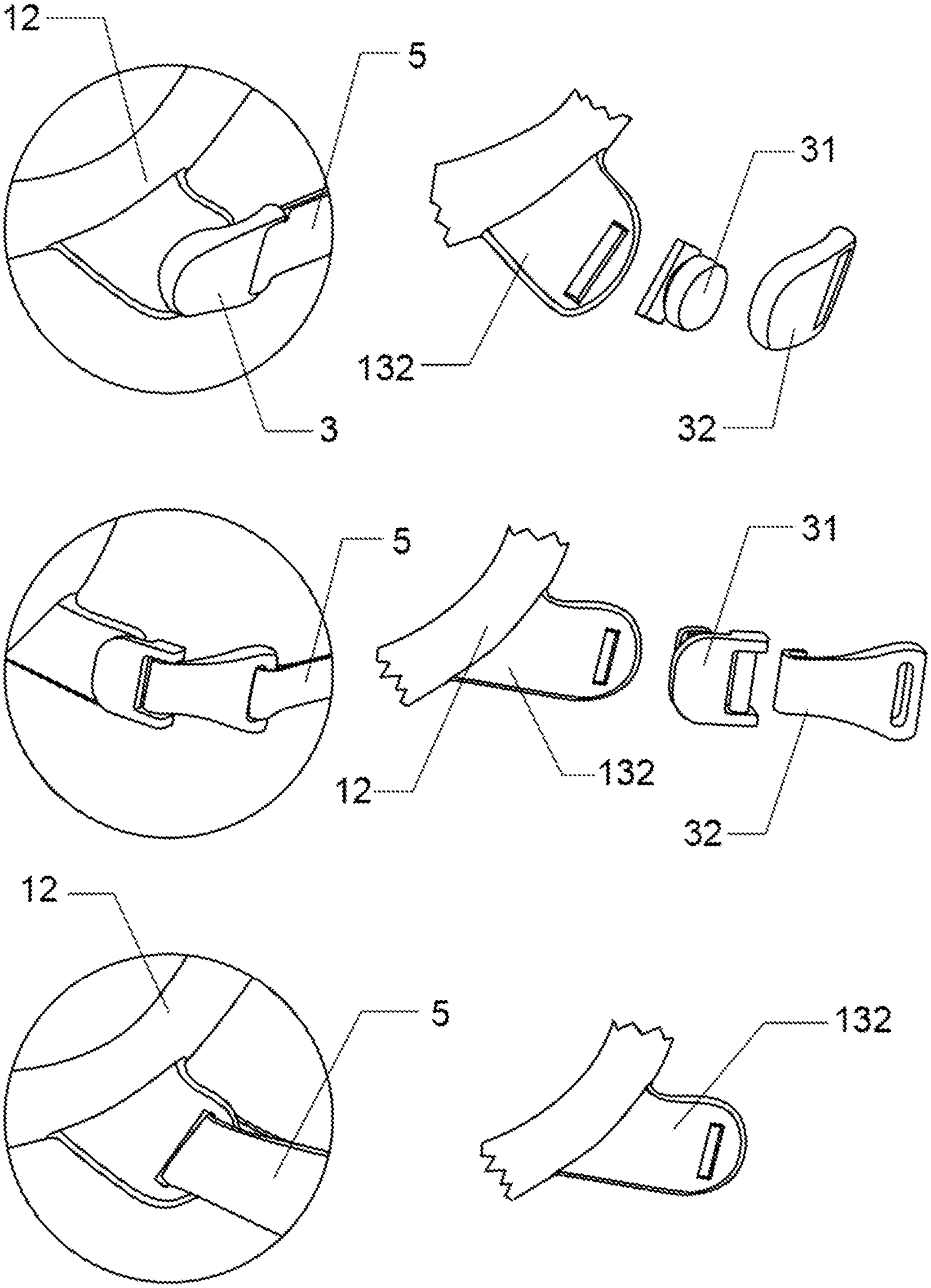
FIG. 11 is a schematic diagram illustrating the connection between the frame assembly and the headgear in accordance with multiple embodiments.

The quick-release component 3, situated in the opening of the wing elements away from the hollow tube 12, establishes a detachable connection with the wing elements. Illustrated in FIG. 11, the quick-release component 3 can be a magnetic clasp or a clip, enabling patients to select among various quick-release components 3 or to forgo them entirely, directly fastening the headgear 5 to the wing elements. Alternatively, the connection between the quick-release component 3 and the wing elements can be made non-detachable through methods such as adhesive bonding. Typically comprised of two sections, the quick-release component 3 has a first section 31, which attaches to the wing element, and a second section 32, which connects to the headgear 5. This arrangement streamlines the attachment of the headgear 5 onto the frame 1 and its subsequent swift separation, thereby easing the wearing process for patients. To ensure a secure connection between the headgear 5 and the frame 1 during use, the quick-release component 3 is engineered with an anti-detachment mechanism. Moreover, in the absence of external force, or when the quick-release component 3 is subjected to a relatively small force, the force binding its first section 31 and second section 32 should exceed the force required to separate the two sections.

Figure 10:
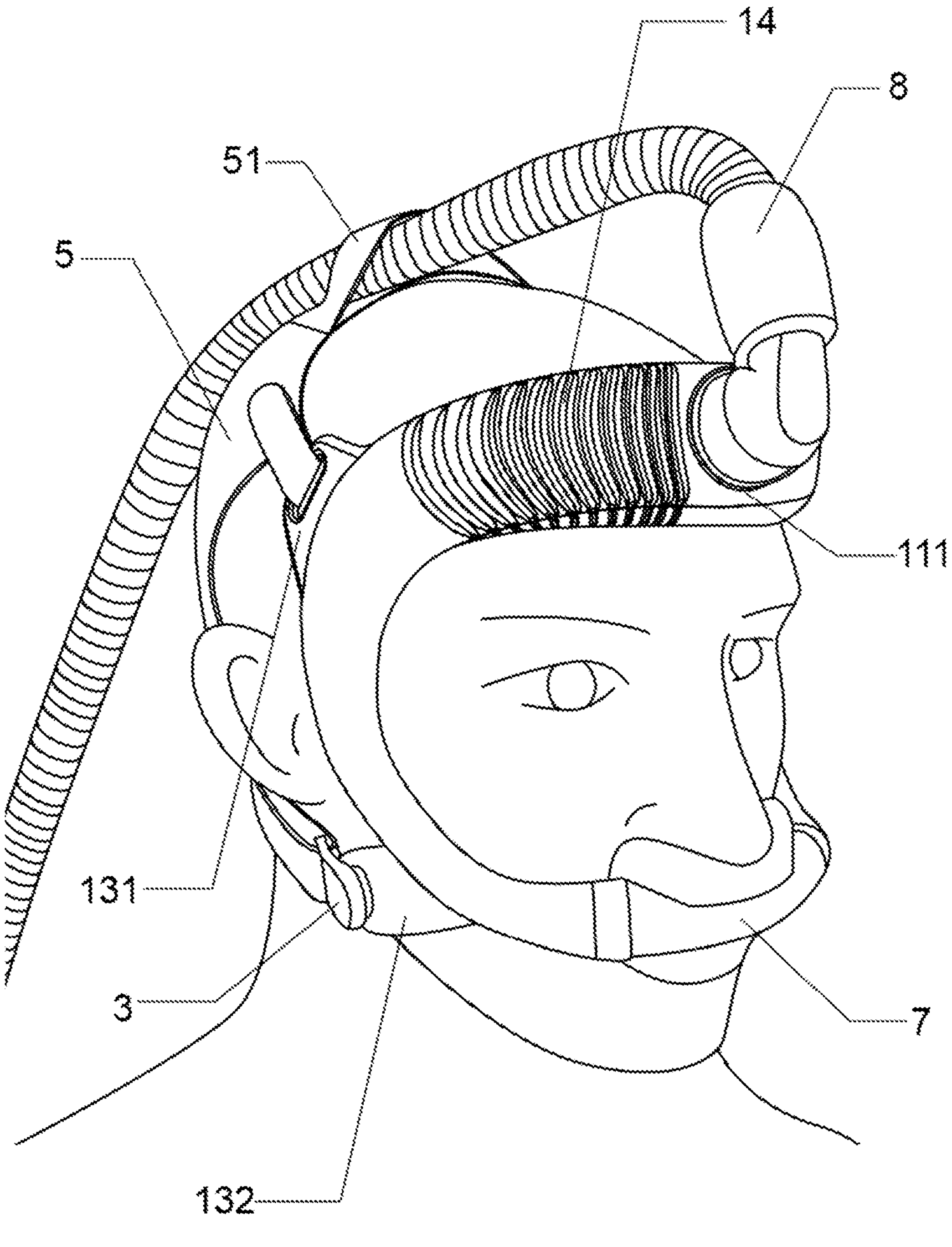
FIG. 10 is a schematic diagram depicting the usage state of the frame assembly in accordance with an example embodiment.

The headgear 5, corresponding to the design of the wing elements of the frame assembly, is at least a three-point headgear for securing the frame 1 to the patient's face, made from textile materials. The headgear 5 is adjustable with mechanisms such as hook-and-loop fasteners, strap buckles, or similar fastening devices, or can also feature automatic adjustment provided by elastic securing devices 51 (like elastic bands), for instance. As depicted in FIG. 10, a preferred embodiment of the headgear 5 has a dual-layer elastic securing device 51 at the top for holding the hose of the gas delivery device 8 that connects to the frame 1, ensuring the hose stays in place and preventing any knotting or entangling during sleep.

Detailed embodiments are presented below to elucidate the configurations of the frame assembly for a ventilator to deliver gas.

Embodiment 1

Figure 2:
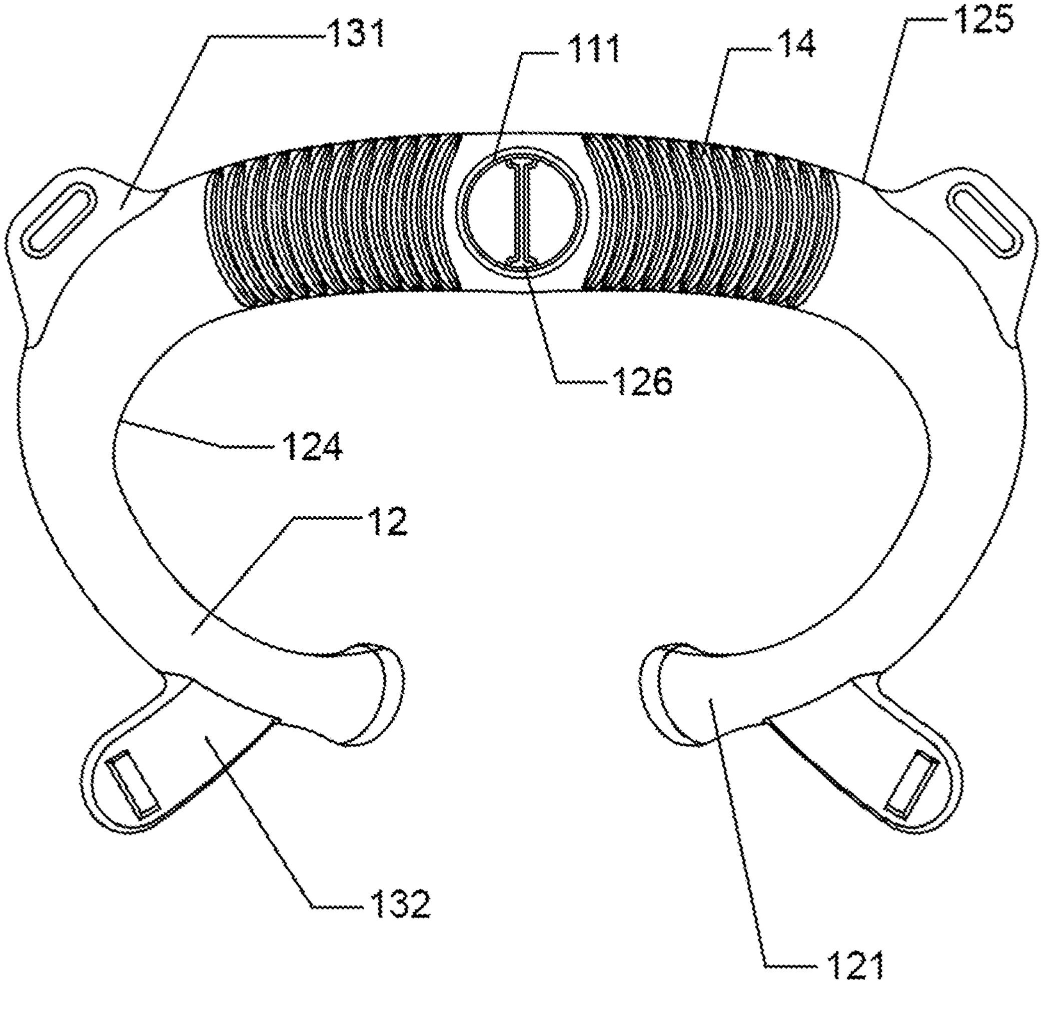
FIG. 2 is a front view of the frame assembly in accordance with an example embodiment.
Figure 3:
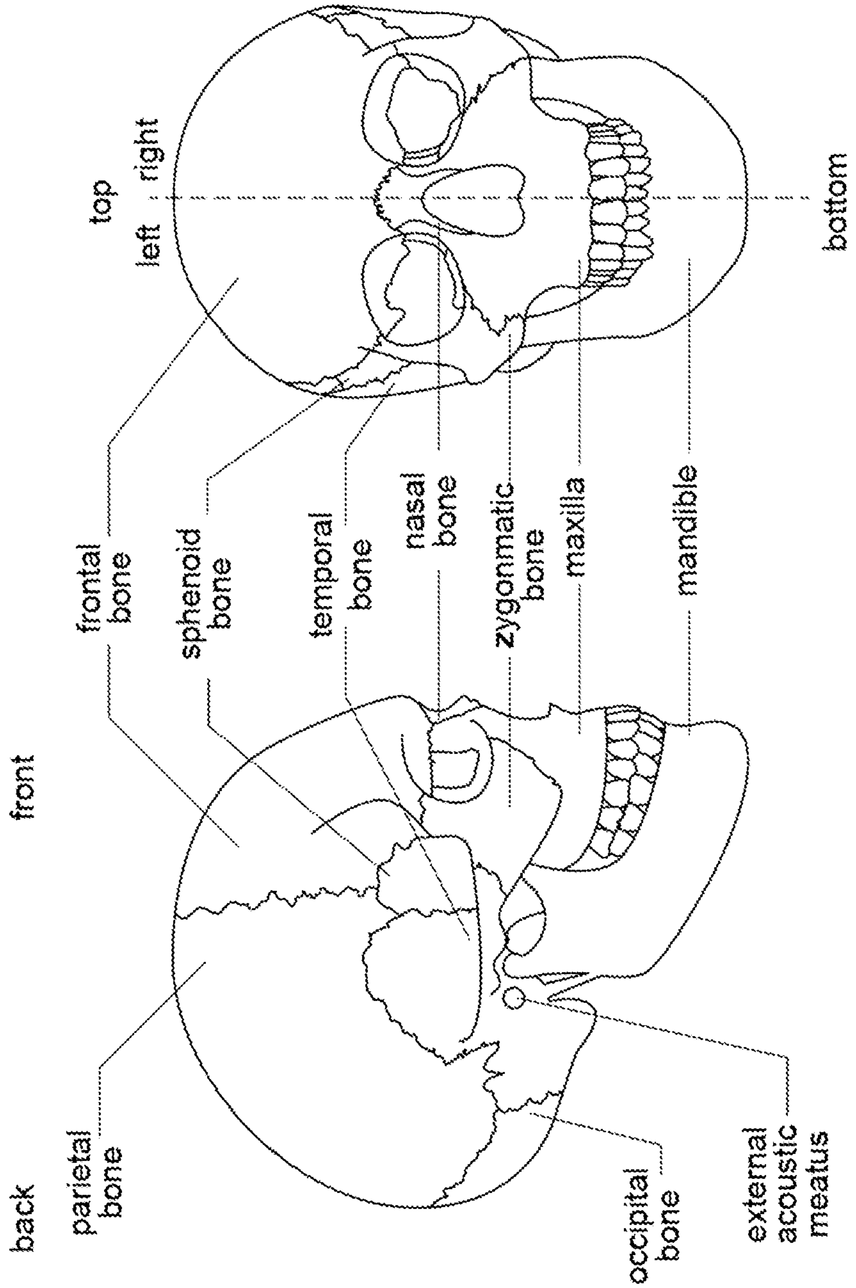
FIG. 3 is a schematic diagram depicting the division of skeletal regions in the human head.

In this embodiment, a frame assembly for a ventilator to deliver gas, configured to deliver positive pressure breathing gas from a flow generator to a patient's airway for the treatment of sleep breathing disorders, can include at least some of the following components, depicted in FIG. 1, FIG. 2, and FIG. 4. The frame assembly has a frame 1 with a first interface 111 set on the forehead of the patient to receive positive pressure breathing gas and two second interfaces 112 near the nasal sides of the patient. The frame 1 has a symmetrical hollow tube 12, connectable to the first interface 111 positioned at the center of the frame 1 and to the second interfaces 112 on each nasal side of the patient, for delivering positive pressure breathing gas from the first interface 111 to the second interfaces 112. The hollow tube 12 has a front wall 121, a back wall 122, and an inner edge 124 and an outer edge 125 formed at the junction of the front wall 121 and the back wall 122. The frame assembly can include a quick-release component 3 to connect to the headgear 5 and the second wing element 132, situated at the end of the second wing element 132 away from the hollow tube 12, and forming a detachable connection with the second wing element 132. Wing elements are configured to connect to a headgear 5 to secure the frame 1 on the patient's face, having a first wing element 131 extending towards the area above the ears on the outer edge 125 of the hollow tube 12 near the first interface 111, and a second wing element 132 extending towards the area below the ears on the outer edge 125 of the hollow tube 12 near the second interface 112. An automatic adjustment mechanism 14 is located on the hollow tube 12 near the first interface 111 without extending beyond the patient's zygomatic bones for automatically adapting the length or width of the hollow tube 12 to accommodate various patients' facial contours.

Figure 7:
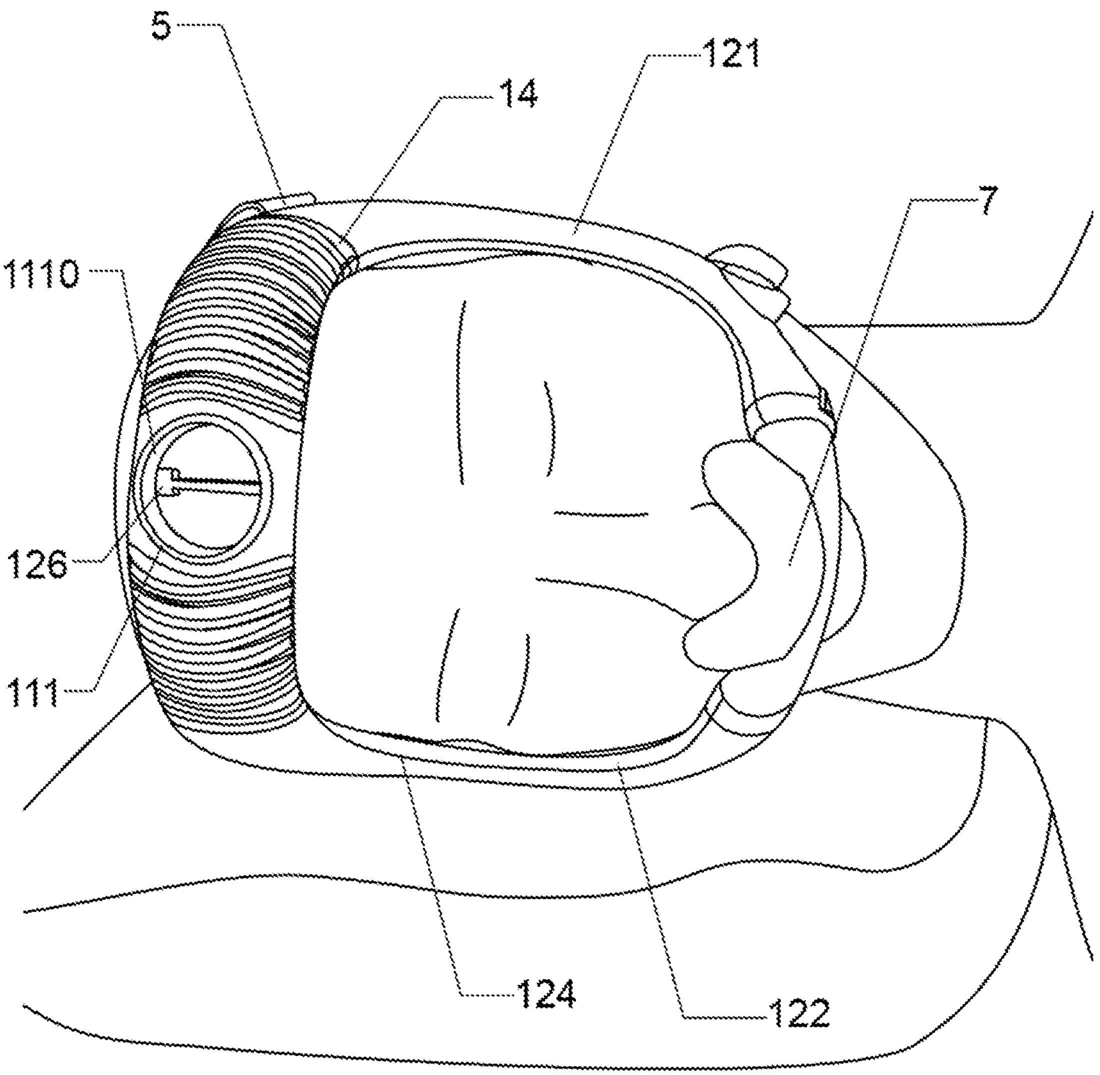
FIG. 7 is a schematic diagram of the frame assembly worn in a lateral position in accordance with an example embodiment.

In this embodiment, the hollow tube 12 extends from a first nasal side of the patient, ascends towards a first temporal region, further rises to the forehead, then extends to a second temporal region and reaches a second nasal side, forming a contour that at least partially encircles the patient's eyes and nose. This means the hollow tube 12 begins at the patient's left nasal side, ascends to the left temporal region, extends across to the midpoint of the forehead, then descends through the right temporal region before circling back to the patient's right nasal side. The pathway outlined by the hollow tube 12 can be defined by either straight segments or smooth, flowing curves. Notably, centering the frame 1 on the patient's forehead and incorporating at least three headgear connection points enhances the stability of the frame's placement. Furthermore, the inclusion of a left and right symmetrical hollow tube 12, connecting both sides of the nose and the forehead, allows the main body of the frame 1 to be near the front side of the patient's head. As depicted in FIG. 7, when the patient is lying on her or his side, the frame 1 steers clear of pronounced facial features like the zygomatic bones and frontal bones, instead conforming closely to the areas with more pliable tissues such as the front of the face and the cheek, which reduces any pressure the head might place on the frame 1 to the fullest extent and maintains proper ventilation while enhancing the comfort of the patient. Additionally, the left and right symmetrical hollow tube 12 serves a fail-safe function, ensuring that if one side is accidentally pressed, the other side remains open to sustain airflow.

In other embodiments, the hollow tube 12 begins with the first nasal side (left side), ascends and courses behind the patient's first ear (left side), loops towards the patient's first temporal region (left side). The hollow tube 12 then descends and passes through the patient's second temporal region (right side), continues behind the patient's second ear (right side), and ultimately circles back to the patient's second nasal side (right side). The space encircled by the hollow tube 12 is not fixed, allowing for variations to maintain effective ventilation and patient comfort.

Embodiment 2

In this embodiment, a frame assembly for a ventilator to deliver gas, configured to deliver positive pressure breathing gas from a flow generator to a patient's airway for the treatment of sleep breathing disorders, can include the following components. The frame assembly has a frame 1 made of continuous hollow elastomer, with a first interface 111 to receive positive pressure breathing gas, a second interface 121 near the nasal side of the patient, and a hollow tube 12 extending between the patient's eyes and ears to connect the first interface 111 and the second interface 112. The hollow tube has a front wall 121 away from the patient's face and a back wall 122 nearer the patient's face. Wing elements are configured to connect to a headgear 5 to secure the frame 1 on the patient's face, having a first wing element 131 on the hollow tube 12 near the first interface 111, and a second wing element 132 on the hollow tube 12 near the second interface 112. An automatic adjustment mechanism 14, located on the hollow tube 12 is used to automatically adapt the length or width of the hollow tube 12 to accommodate the facial contours of different patients.

Figure 15:
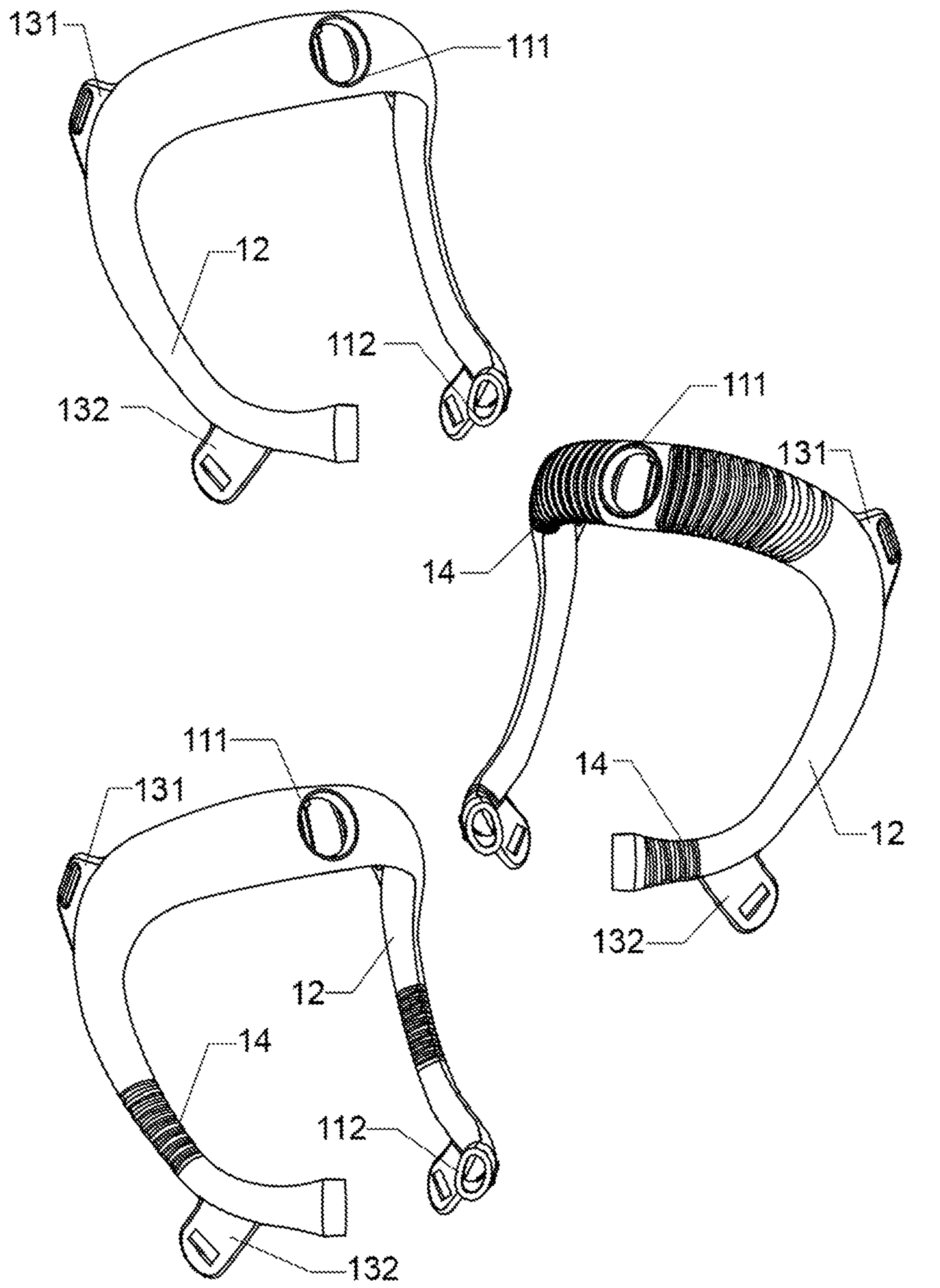
FIG. 15 is a schematic diagram illustrating the position of the automatic adjustment mechanism in the frame assembly in accordance with Embodiment 2.

Embodiment 2 differs from Embodiment 1 in the placement of the automatic adjustment mechanism 14. As shown in FIG. 15, the automatic adjustment mechanism 14 is located near the second interface 112 and is used to adjust the height distance between the first interface 111 and the second interface 112, accommodating the varying distances from the nose to the forehead among patients. In another implementation, the automatic adjustment mechanism 14 can be located at various positions, allowing for multiple adjustments, thereby enhancing conformity to diverse facial contours. In yet another embodiment, the hollow tube 12 does not incorporate an automatic adjustment mechanism 14. Instead, the frame 1 is available in a range of distinct sizes to accommodate different patients.

Embodiment 3

Figure 16:
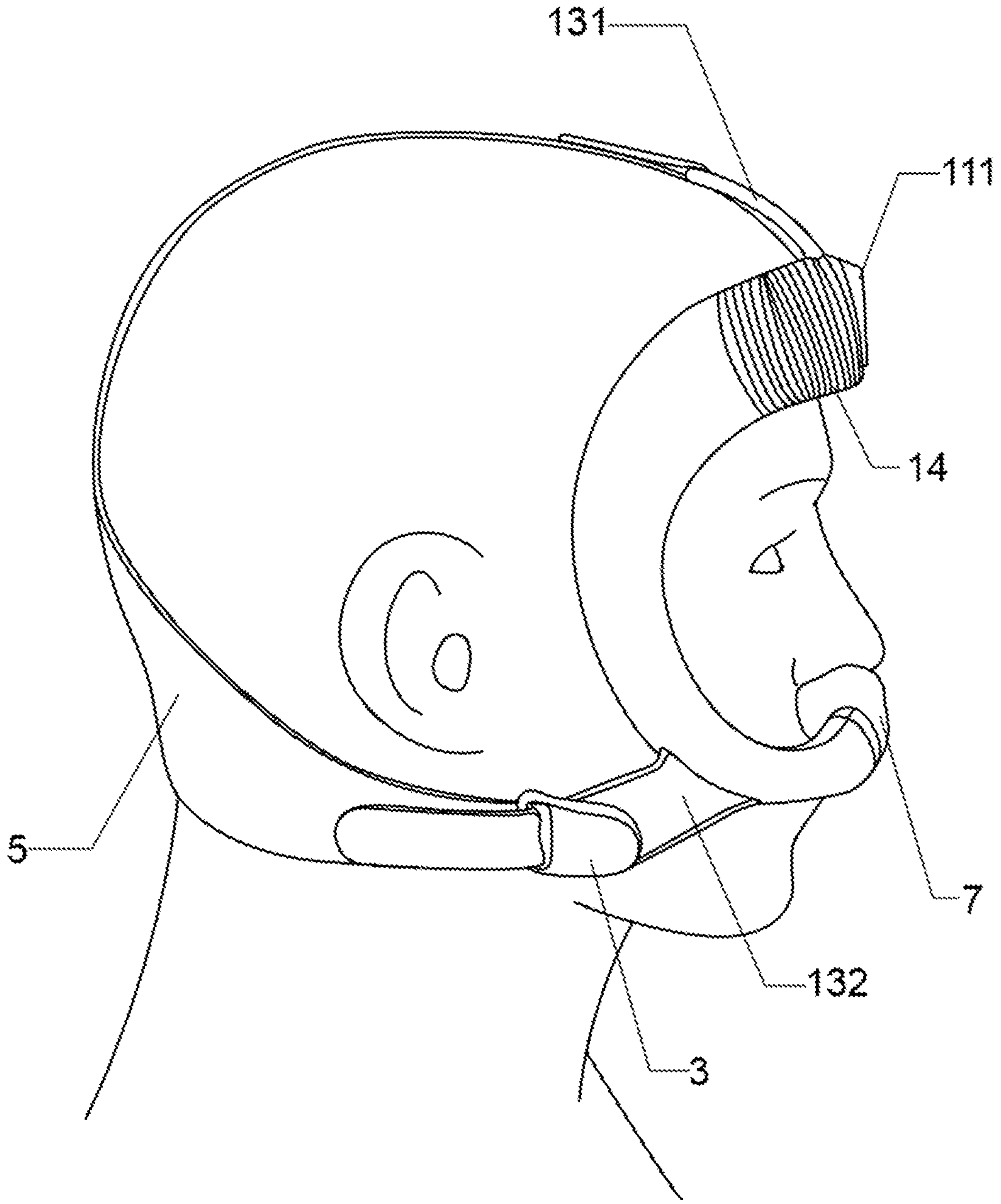
FIG. 16 is a left-side view of the frame assembly in its worn state in accordance with Embodiment 3.

In this embodiment, a frame assembly for a ventilator to deliver gas, configured to deliver positive pressure breathing gas from a flow generator to a patient's airway for the treatment of sleep breathing disorders, can include at least some of the following components. The frame assembly has a frame 1, with a first interface 111 on the forehead of the patient to receive positive pressure breathing gas and two second interfaces 112 near the patient's nasal sides. The frame 1 has a symmetrical hollow tube 12, connectable to the first interface 111 positioned at the center of the frame 1 and to the second interfaces 112 on each nasal side of the patient, for delivering positive pressure breathing gas from the first interface 111 to the second interfaces 112. The hollow tube 12 has a front wall 121, a back wall 122, an inner edge 124 and an outer edge 125 formed at the junction of the front wall 121 and the back wall 122. Wing elements are configured to connect to a headgear 5 to secure the frame 1 on the patient's face, having a first wing element 131 set on the center of the frame 1 and on the outer edge 125 of the hollow tube 12 extending upward and backward over the head, and the second wing elements 132 extending towards the area below the ears on the outer edge 125 of the hollow tube 12 near the second interface 112. Embodiment 3 differs from Embodiment 1 in the quantity and location of the first wing element 131. As illustrated in FIG. 16 which is a left-side view of the frame assembly in its worn state, the first wing element 131 is positioned at the center of the frame 1, extending upward and backward over the head from the outer edge 125 of the hollow tube 12. This positioning exerts an upward and backward pulling force on the frame 1, securing the frame 1 at the forehead. The second wing elements 132 are symmetrically placed on both sides of the second interfaces 112, with the points where the wing elements are located forming an isosceles triangle. The headgear 5 extends from the top of the head towards the back part of the head, at least partially encircling the back of the head, and then extends towards the area below the ears, thereby creating a triangular shape. This design with its reduced coverage area around the head and improved breathability presents a distinct advantage in comfort over the more traditional four-point headgear systems.

Embodiment 4

Figure 17:
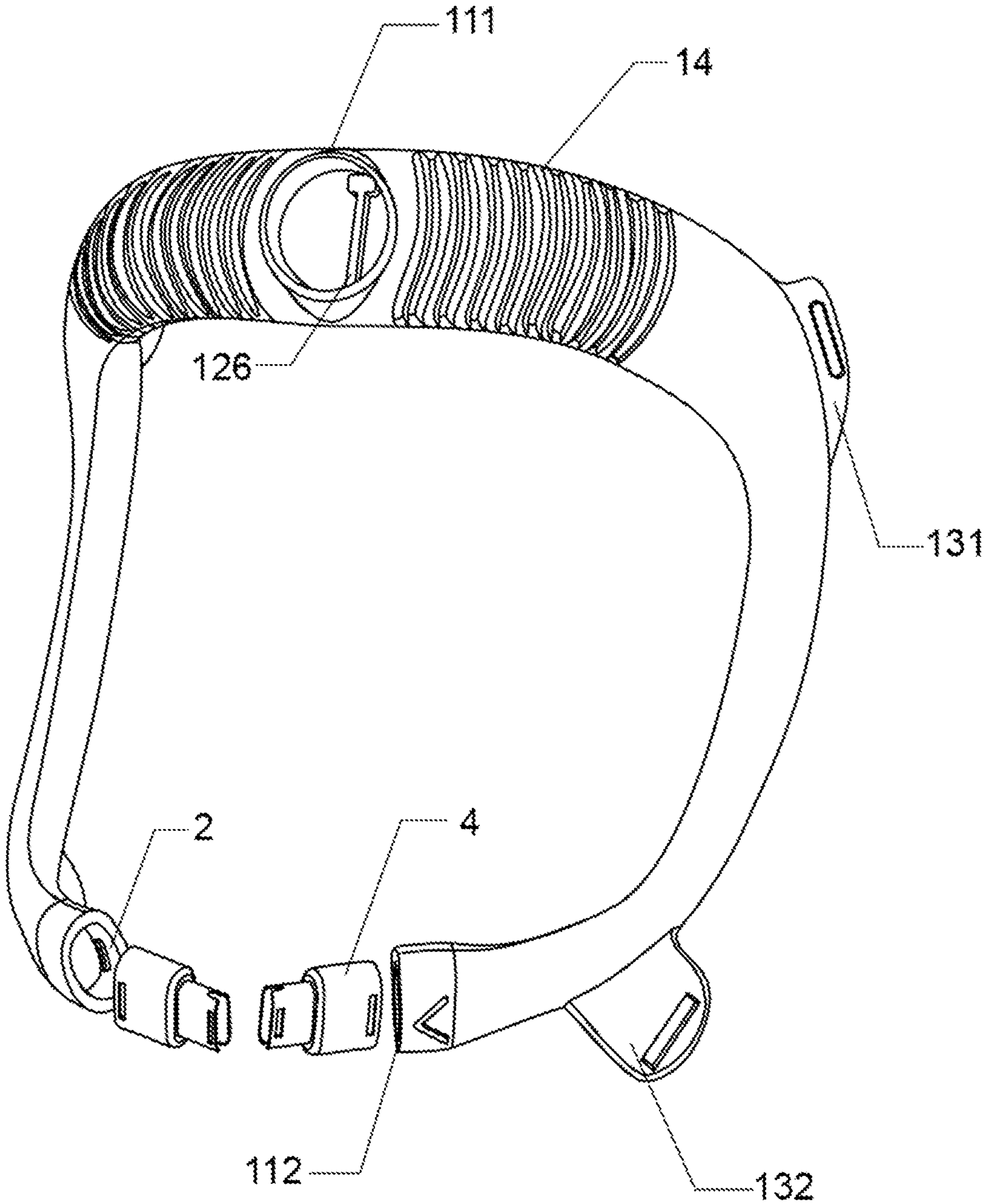
FIG. 17 is an exploded schematic diagram of the frame assembly and the connecting component in accordance with Embodiment 4.
Figure 18:
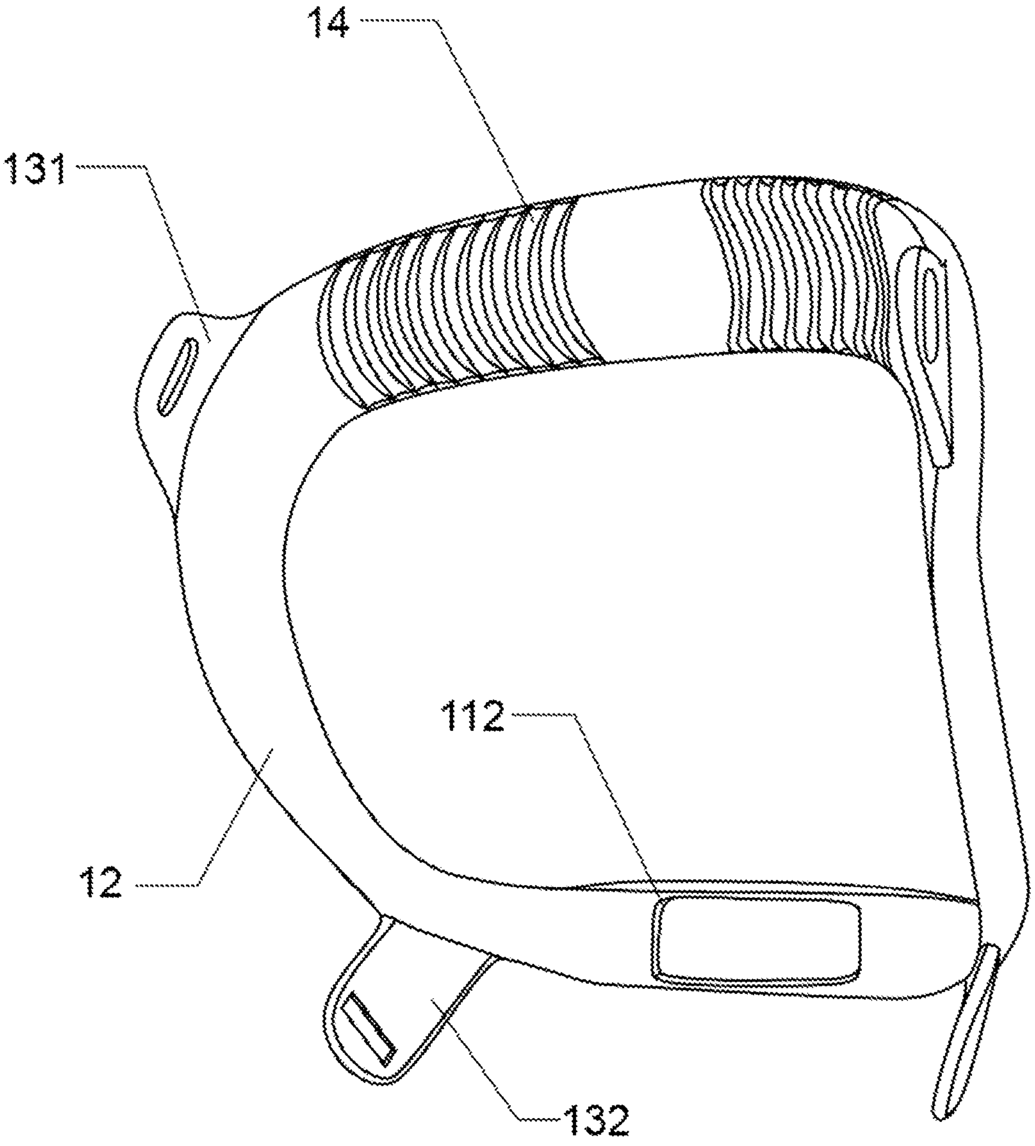
FIG. 18 is a schematic diagram of the second interface of the frame assembly in accordance with Embodiment 5.

In this embodiment, a frame assembly for a ventilator to deliver gas, configured to deliver positive pressure breathing gas from a flow generator to a patient's airway for the treatment of sleep breathing disorders, can include at least some of the following components. The frame assembly has a frame 1, made of continuous hollow elastomer, having a first interface 111 to receive positive pressure breathing gas and a second interface 112 near a nasal side of the patient, and a hollow tube 12, extending between the patient's eyes and ears to connect the first interface 111 and the second interface 112. The hollow tube 12 extends from a first nasal side of the patient, ascends towards a first temporal region, further reaches a second temporal region and reaches a second nasal side of the patient, forming a contour that at least partially encircles the patient's eyes and nose. The frame assembly also has a connecting component 4. As shown in FIG. 17, the connecting component 4 is located between a rigid interface 2 and a patient interface cushion 7. The connecting component 4 has a first port to connect to the rigid interface 2 and a second port to connect to a patient interface cushion 7, forming a detachable connection with both the rigid interface 2 and the patient interface cushion 7. The first port of the connecting component 4 corresponds to the rigid interface 2 in shape and size, while the second port of the connecting component 4 corresponds to the patient interface cushion 7 in shape and size. While the first port of the connecting components 4 remains unchanged, the second port can be designed according to the desired interface of the patient interface cushion 7, which enables a single frame 1 to accommodate different types of patient interface cushions 7, enhancing the design flexibility of the patient interface cushion 7. For example, in the case of the patient interface cushion 7 employing a snap-fit male/female connector, the connecting component 4 is tailored to correspond with this configuration. Similarly, patient interface cushions 7 with magnetic or rotational interfaces can be accommodated by simply adjusting the second port of the connecting component 4, eliminating the need to alter the frame 1 itself. A straightforward substitution of the connecting component 4 is all that's required. Furthermore, the connecting component 4 is capable of supporting additional features, which is used to adjust the width of the frame 1 by employing connecting components 4 of various lengths, or to integrate supplementary functionalities, such as oxygen ports, temperature sensors, pressure sensors, and more, facilitating the monitoring of pressurized airflow conditions. The system is even compatible with advanced safety features, including the addition of an anti-asphyxiation valve, to accommodate patient interface cushions 7 for oronasal coverage.

Embodiment 5

In this embodiment, a frame assembly for a ventilator to deliver gas, configured to deliver positive pressure breathing gas from a flow generator to a patient's airway for the treatment of sleep breathing disorders, can include at least some of the following components. The frame assembly has a frame 1, made of continuous hollow elastomer, having a first interface 111 to receive positive pressure breathing gas and a second interface 112 near the nose of the patient, and a hollow tube 12, extending between the patient's eye and ears to connect the first interface 111 and the second interface 112. Wing elements are configured to connect to a headgear 5 to secure the frame 1 on the patient's face, having a first wing element 131 on an outer edge 125 of the hollow tube 12 near the first interface 111, and a second wing element 132 on the outer edge 125 of the hollow tube 12 near the second interface 112, with the first interface 111 penetrating through the front wall 121 of the hollow tube 12 and the second interface 112 penetrating through the back wall 122 of the hollow tube 12. In this embodiment, there is only one second interface 112 for connection to the patient interface cushion 7. And the second interface 112 can be connected to the patient interface cushion 7 in several methods. One approach is through the placement of a rigid interface 2 on the second interface 112, thereby creating a detachable connection with the patient interface cushion 7 via the rigid interface 2. Alternatively, the patient interface cushion 7 can incorporate a section made from a rigid material, marginally exceeding the size of the second interface 112, which holds the patient interface cushion 7 in place by the deformable properties of the second interface 112 which is made of elastomer. Moreover, in this embodiment, the front wall 121 of the hollow tube 12, near the second interface 112, can have exhaust holes that are used to facilitate the efficient discharge of exhaled gas during patient treatment.

Embodiment 6

Figure 19:
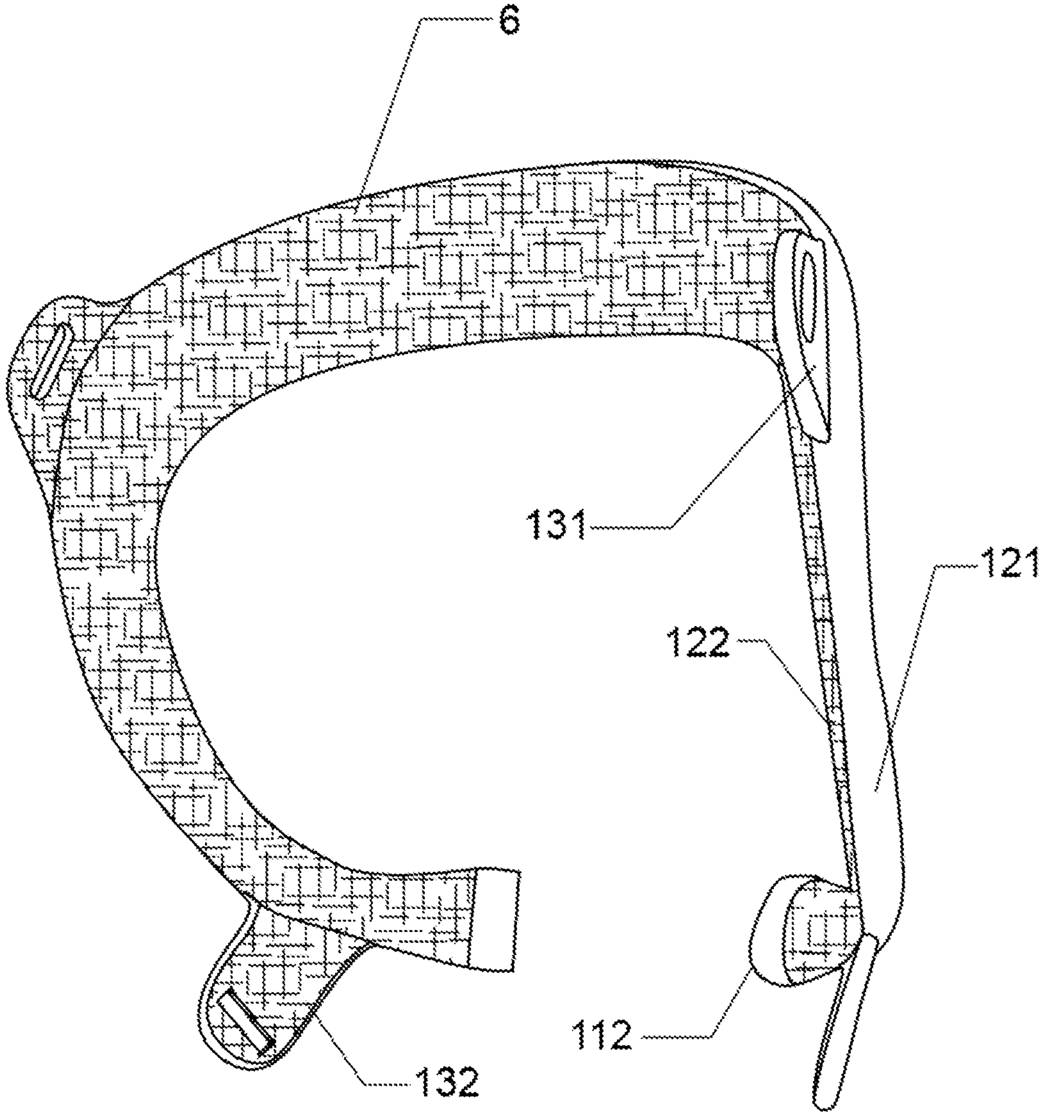
FIG. 19 is a schematic diagram of the frame assembly with a comfort layer in accordance with Embodiment 6.

In this embodiment, a frame assembly for a ventilator to deliver gas, configured to deliver positive pressure breathing gas from a flow generator to a patient's airway for the treatment of sleep breathing disorders, can include the following components. The frame assembly has a frame 1, made of continuous hollow elastomer, having a first interface 111 to receive positive pressure breathing gas and a second interface 112 near a nasal side of the patient, and a hollow tube 12, extending between the patient's eye and ear to connect the first interface 111 and the second interface 112. Wing elements are configured to connect to a headgear 5 to secure the frame 1 on the patient's face, having a first wing element 131 on the hollow tube 12 near the first interface 111, and a second wing element 132 on the hollow tube 12 near the second interface 112. A comfort layer 6 is positioned on at least a portion of the back wall 122 of the hollow tube 12, conforming to the patient's face. Embodiment 6, compared to Embodiment 1, includes the additional feature of the comfort layer 6. As depicted in FIG. 19, the frame assembly's close fit to the patient's face can cause pressure, potentially leading to discomfort or red marks for some patients. Therefore, a comfort layer 6 is set on the back wall 122 of the hollow tube 12 that comes into contact with the face. The comfort layer 6, composed of materials like textile fabrics, foam, or a combination thereof, serves primarily to heighten comfort during wear and make the assembly breathe better. Notably, the comfort layer 6 excels at absorbing sweat, thereby enhancing the overall patient experience. In another implementation, the comfort layer 6 can be made of a gel material that is softer than the frame 1. The comfort layer 6 can be externally attached to the frame 1, secured by means such as hook-and-loop fasteners, strap buckles, double-sided adhesive tapes, or removable glues. Alternatively, the comfort layer 6 can also be affixed to the frame 1 using adhesive bonding, heat pressing, ultrasonic welding, or even be molded directly onto the frame 1, creating a seamless, unified component.

The benefits of the frame assembly for a ventilator to deliver gas provided by this disclosure can at least include:

1) The frame assembly of this disclosure is more stable than existing frames which have tubes with the air inlet set atop the patient's head. Existing tubular frames are susceptible to dislocation, prompted by their inherent weight coupled with the traction from the gas delivery device, particularly when the patient assumes a supine posture. This instability often results in the inadvertent displacement of the patient interface cushion, leading to gas leakage. In contrast, the frame 1 assembly provided by this disclosure envelops the patient's face, placing the air inlet (the first interface 111) at the forehead. This orientation capitalizes on the supportive force exerted by the forehead in a supine position, counteracting the gravitational pull of the frame 1, which prevents the frame 1 from descending and disrupting the positioning of the patient interface cushion 7, thereby avoiding gas leakage. Moreover, the gas interface of the frame 1 set directly on the patient's face allows patients to accurately discern the location of the gas interface with a mirror, which is an improvement over traditional designs that situate the gas interface on the headgear 5 since this design simplifies the installation of the elbow or other gas delivery devices 8. Besides, the frame 1 has an automatic adjustment mechanism 14 that allows it to automatically adapt to the patient's facial shape when worn in response to the dual effects of gravity and the pulling force, ensuring a better fit that maintains intimate contact with the patient's facial contours.

2) The frame assembly of this disclosure has at least three headgear connection points, a design choice that improves its stability and airtightness compared to existing tubular frames with two connection points. Existing frame designs, which commonly have only two pulling forces exerted on the frame 1 above the ears towards the back part of the head, inadequately counteract the frame 1's tendency to slide downward. When patients lie supine, the backward pull of the headgear on the frame makes it easier to pull the frame off the top of the head. Moreover, due to the absence of additional pulling forces surrounding the patient interface cushion, the patient interface cushion can easily shift away from the patient's airway, particularly when the patient is lying on her or his side. In contrast, the frame assembly presented herein has at least three pulling force points. One of the pulling forces comes from the frame 1's upper part, exerting forces on the upper part of the frame 1 towards the upper and back parts of the head to combat gravitational pull so that the frame 1 does not slip, ensuring the upper part of the frame 1 fits against the facial contours of patients. Additionally, two pulling force points are applied to the frame 1 near the nasal sides, pulling towards the back part of the head. This helps secure a snugger fit against the face and, indirectly, pulling the patient interface cushion 7 into closer proximity with the nose. With three connection points for the headgear 5 to encapsulate the head more securely, the nocturnal movements or variations in facial muscles exert minimal disruption to the stability of the frame assembly and the positioning of the patient interface cushion 7. The headgear has an elastic securing device 51, stabilizing the breathing tube on the patient's head, further bolstering the overall stability and dependability of the therapeutic assembly. The placement of the gas delivery device 8 on the head, secured firmly with the headgear 5, reduces concerns of tube detachment or entanglement during sleep. For added convenience during disassembly, the frame assembly incorporates a quick-release component 3 which enables patients to swiftly separate the frame 1 from the headgear 5, avoiding the need to repeatedly adjust the length of the headgear 5.

3) The frame assembly of this disclosure has a smoother airflow, which is an improvement over existing designs where the frame extends from the patient's nasal side to the top of the head. Existing frames, although configured to bypass the zygomatic bone's apex, unavoidably cross over the lateral bones of the head. When the patient is lying on her or his side, the tube on one side is easily pressed, disrupting airflow to the patient's airway, and diminishing sleep quality. Conversely, the frame 1 of this disclosure is set at the front of the patient's face, tactically avoiding protruding skeletal structures, such as the zygomatic bones and the forehead. As a patient or user lies on her or his side, the patient's or user's cheeks, which are the softer portion of the face, contact the frame, which is less likely to press the tube and helps maintain smooth airflow to the maximum extent throughout the therapeutic session.

4) The frame assembly of this disclosure incorporates connecting components 4. With the replacement of connecting components 4, the connection of a single frame with different types of patient interface cushions 7 can be achieved, which allows patients to select cushions that best meet their needs. For example, patient interface cushions 7 with a male connector can be paired with connecting components 4 featuring a female counterpart, and vice versa, patient interface cushions with a female connector can also be paired with connecting components with a male connector. This compatibility achieves a modular function without having to replace the entire frame or patient interface cushion and it requires merely the substitution of a minor component, providing better choices for both manufacturers and patients. For manufacturers, they are no longer confined to interfaces that connect with the frame when designing patient interface cushions, and have more space for pioneering designs. Patients, on the other hand, can opt for patient interface cushions 7 of different types, structures, and functionalities. Furthermore, this approach of interchangeable connections between multiple frames 1 and patient interface cushions 7 presents an environmental upside. Separately designed and replaceable connecting components 4 bring reduced consumption of raw materials, effectively conserving existing resources for sustainable energy use, minimizing production waste, and reducing carbon emissions and climate change.

5) In comparison to current non-tubular frames that create a seal around the patient's airway, the frame assembly of this disclosure offers an expanded area of contact with the face, made from elastomer, which helps distribute the force applied by the headgear 5. This results in reduced pressure on the face, preventing squeezing of the patient's face. Furthermore, unlike existing methods, this design locates the gas interface away from the patient's face, mitigating disruptions from exhaust airflow and diminishing noise sensitivity, thereby fostering a more serene sleeping experience for the patient.

The technical features referenced in the preceding embodiments are subject to various combinations. For conciseness, not every conceivable combination has been enumerated in the descriptions. Nevertheless, provided there is no contradiction in these combinations, they are to be regarded as included within the scope of this disclosure.

The embodiments presented here merely represent several embodiments of this disclosure, offering detailed and explicit descriptions. These should not be construed as confining the scope of the associated patent. It must be noted that those proficient in the pertinent domain can effectuate several modifications and enhancements, consistent with the foundational principles and essence of the disclosure. Such adaptations are encompassed within the protection scope of this disclosure. Thus, the definitive protection scope for the patent concerning this disclosure should be adjudicated based on the claims.

It must be noted that as used herein and in the appended claims, the singular forms "a", "an", and "the" include their plural equivalents, unless the context clearly dictates otherwise.

The invention claimed is:

1. A frame assembly for a ventilator to deliver gas, configured to deliver positive pressure breathing gas from a flow generator to an airway of a patient for treatment of sleep breathing disorders, the frame assembly for the ventilator to deliver gas comprising:

a frame comprising:

a first interface configured to be provided on a forehead of the patient to receive positive pressure breathing gas, two second interfaces configured to be provided on, respectively, a first nasal side and a second nasal side of the patient, and a symmetrical hollow tube configured to be connected to the first interface positioned at a center of the frame and to the two second interfaces on both the first and the second nasal sides of the patient, the symmetrical hollow tube configured to deliver positive pressure breathing gas from the first interface to the two second interfaces, the hollow tube comprising:

a front wall, a back wall, an inner edge, and an outer edge formed at a junction of the front wall and the back wall;

wing elements, integrally formed with the frame and made of silicone with a hardness of at or between 30 A to 70 A on a Shore scale, configured to connect a headgear to secure the frame on a face of the patient, the wing elements are configured to extend towards an area above ears of the patient, wherein the wing elements have a force applied to the frame that is configured to extend towards a back part of the patient's head to draw the frame against the patient's face, and wherein the hollow tube is configured to extend from the first nasal side of the patient, to ascend towards a first temporal region of the patient, to further rise to a mid-point of the forehead of the patient at which the positive pressure breathing gas is received, to extend to a second temporal region of the patient, to reach the second nasal side of the patient, and to form a contour to at least partially encircle a nose and eyes of the patient.

2. The frame assembly for the ventilator to deliver gas according to claim 1, wherein the wing elements have at least one opening to connect to the headgear, and the wing elements have at least one opening to connect to a quick-release component.

3. The frame assembly for the ventilator to deliver gas according to claim 1, wherein the frame assembly further includes an automatic adjustment mechanism, which includes concave and convex sections of an elastomeric material, located on the hollow tube near the first interface to automatically adapt a length or a width of the hollow tube to accommodate facial contours of different patients.

4. A frame assembly for a ventilator to deliver gas, configured to deliver positive pressure breathing gas from a flow generator to an airway of a patient for treatment of sleep breathing disorders, the frame assembly for the ventilator to deliver gas comprising:

a frame comprising:

a first interface configured to be provided on a forehead of the patient to receive positive pressure breathing gas, two second interfaces configured to be provided on, respectively, a first nasal side and a second nasal side of the patient, and a symmetrical hollow tube, configured to be connected to the first interface positioned at a center of the frame and to the two second interfaces on both the first and the second nasal sides of the patient, rising to a mid-point of the forehead of the patient at which the positive pressure breathing gas is received, the symmetrical hollow tube configured to deliver positive pressure breathing gas from the first interface to the two second interfaces, the hollow tube comprising:

a front wall, a back wall, and an inner edge and an outer edge formed at a junction of the front wall and the back wall;

wing elements, integrally formed with the frame and made of silicone with a hardness of at or between 30 A to 70 A on a Shore scale, configured to connect to a headgear to secure the frame on a face of the patient, the wing elements are configured to extend towards an area above ears of the patient, wherein the wing elements have a force applied to the frame that is configured to extend towards a back part of the patient's head to draw the frame against the patient's face, a rigid interface configured to detachably connect to a patient interface cushion and being provided at an end of the second interface of the frame to form an undetachable connection with the two second interfaces.

5. The frame assembly for the ventilator to deliver gas according to claim 4, wherein the frame assembly further comprise:

a quick-release component configured to connect the headgear to the wing elements, provided at an end of the wing elements away from the hollow tube to form a detachable connection with the wing elements.

6. The frame assembly for the ventilator to deliver gas according to claim 4, wherein the rigid interface is connectable to the two second interfaces through co-molding or welding.

7. The frame assembly for the ventilator to deliver gas according to claim 4, wherein the rigid interface has at least one protrusion to connect to the patient interface cushion.

8. The frame assembly for the ventilator to deliver gas according to claim 4, wherein the frame assembly further comprises:

a connecting component, the connecting component having a first port to connect to the rigid interface and a second port to connect to the patient interface cushion, the connecting component configured to form a detachable connection with both the rigid interface and the patient interface cushion.

9. The frame assembly for the ventilator to deliver gas according to claim 8, wherein the first port of the connecting component corresponds to the rigid interface in shape and size, and the second port of the connecting component corresponds to the patient interface cushion in shape and size.

10. A frame assembly for a ventilator to deliver gas, configured to deliver positive pressure breathing gas from a flow generator to an airway of a patient for treatment of sleep breathing disorders, the frame assembly for the ventilator to deliver gas comprising:

a frame, made of continuous hollow elastomer, the frame comprising:

a first interface to receive positive pressure breathing gas, a second interface configured to be provided near a nasal side of the patient, and a hollow tube configured to extend from the patient's eye and ear on each side to connect to both the first interface and the second interface and to rise to a mid-point of the forehead of the patient at which the positive pressure breathing gas is received;

wing elements, integrally formed with the frame and made of silicone with a hardness of at or between 30 A to 70 A on a Shore scale, configured to connect to a headgear to secure the frame on a face of the patient, the wing elements are configured to extend from the hollow tube towards an area above ears and have at least one opening to connect to the headgear to provide the frame with a pulling force towards a back part of a head when in use, the pulling force being configured to draw the frame against the patient's face and pull a patient interface cushion nearer the airway of the patient; and wherein the hollow tube comprises:

a support portion on an inner wall corresponding to the first interface configured to prevent a gas delivery device from bottoming out and sealing off a pressurized airflow when connected to the first interface.

11. The frame assembly for the ventilator to deliver gas according to claim 10, wherein the first interface comprises an annular wall that extends into an interior cavity of the hollow tube to strengthen a connection and to ensure an effective seal with the gas delivery device.

12. The frame assembly for the ventilator to deliver gas according to claim 10, wherein the hollow tube further comprises a front wall that is provided to be away from the face of the patient and a back wall near the face of the patient, and the first interface is configured to penetrate through the front wall of the hollow tube.

13. The frame assembly for the ventilator to deliver gas according to claim 10, wherein the hollow tube is configured to extend from a first nasal side of the patient, to ascend towards a first temporal region, to extend to a second temporal region and to reach a second nasal side to form a contour to at least partially encircle a nose and eyes of the patient.

14. The frame assembly for the ventilator to deliver gas according to claim 10, wherein the support portion is a strip-like protrusion formed on the inner wall of the hollow tube, and a length of the support portion exceeds a distance between intersecting points at which the first interface meets a straight line extending from the support portion in a lengthwise direction.

15. A frame assembly for a ventilator to deliver gas, configured to deliver positive pressure breathing gas from a flow generator to an airway of a patient for treatment of sleep breathing disorders, the frame assembly for the ventilator to deliver gas comprising:

a frame, comprising:

a first interface to receive positive pressure breathing gas, two second interfaces, each configured to be respectively provided near a first nasal side and a second nasal side of the patient, and a symmetrical hollow tube configured to be connected to the first interface positioned at a center of the frame and to the two second interfaces on both the first and the second nasal sides of the patient, rising to a mid-point of the forehead of the patient at which the positive pressure breathing gas is received, the symmetrical hollow tube configured to deliver positive pressure breathing gas from the first interface to the two second interfaces, with the hollow tube comprising:

a front wall, a back wall, an inner edge, and an outer edge formed at a junction of the front wall and the back wall;

an automatic adjustment mechanism configured to be provided on the hollow tube near the first interface, to not extend beyond zygomatic bones of the patient, and to automatically adapt a length or a width of the hollow tube to accommodate facial contours of different patients, wherein the automatic adjustment mechanism includes concave and convex sections of an elastomeric material;

wing elements, integrally formed with the frame and made of silicone with a hardness of at or between 30 A to 70 A on a Shore scale, configured to connect to a headgear to secure the frame on a face of the patient, the wing are configured to extend towards an area above ears wherein the wing elements have a force applied to the frame that is configured to extend towards a back part of the patient's head to draw the frame against the patient's face, wherein the hollow tube is configured to extend from the first nasal side of the patient, to ascend towards a first temporal region, to extend to a second temporal region and to the second nasal side, to form a contour to at least partially encircle a nose and eyes of the patient.

16. The frame assembly for the ventilator to deliver gas according to claim 15, wherein the automatic adjustment mechanism includes folded walls made from elastomeric material with multiple concave sections and convex sections.

17. The frame assembly for the ventilator to deliver gas according to claim 15, wherein the front wall of the hollow tube is arc-shaped, and the back wall is of a flat-plate type.

18. The frame assembly for the ventilator to deliver gas according to claim 15, wherein the quick-release component has a form of a magnetic clasp or a clip.

19. The frame assembly for the ventilator to deliver gas according to claim 15, wherein an end of the hollow tube near the first interface is larger than an end of the hollow tube near the two second interfaces.

20. The frame assembly for the ventilator to deliver gas according to claim 15, wherein the automatic adjustment mechanism is integrally formed with the hollow tube and is made of silicone with a hardness of at or between 30 A to 70 A on a Shore scale.

* * * * *